US006875753B1

(12) United States Patent
Pilarski

(10) Patent No.: US 6,875,753 B1
(45) Date of Patent: Apr. 5, 2005

(54) METHODS FOR CELL MOBILIZATION USING IN VIVO TREATMENT WITH HYALURONAN (HA)

(75) Inventor: Linda May Pilarski, Stony Plain (CA)

(73) Assignee: The Governors of the University of Alberta, Edmonton (CA)

( * ) Notice: Subject to any disclaimer, the term of this patent is extended or adjusted under 35 U.S.C. 154(b) by 0 days.

(21) Appl. No.: 09/142,557

(22) PCT Filed: Mar. 12, 1997

(86) PCT No.: PCT/CA97/00172

§ 371 (c)(1),
(2), (4) Date: Sep. 11, 1998

(87) PCT Pub. No.: WO97/33592

PCT Pub. Date: Sep. 18, 1997

Related U.S. Application Data
(60) Provisional application No. 60/013,401, filed on Mar. 14, 1996.

(30) Foreign Application Priority Data

Apr. 2, 1996 (CA) ............................................. 2173272

(51) Int. Cl.[7] ............................................. A61K 31/728
(52) U.S. Cl. ........................................................ 514/54
(58) Field of Search ............................................. 514/54

(56) References Cited

U.S. PATENT DOCUMENTS

| | | | |
|---|---|---|---|
| 4,141,973 A | 2/1979 | Balazs ........................ | 424/180 |
| 4,725,585 A | 2/1988 | Wenge et al. .................. | 514/54 |
| 5,079,236 A | 1/1992 | Drizen et al. | |
| 5,646,129 A | 7/1997 | Callegaro et al. | |
| 5,817,644 A | 10/1998 | Gustafson | |
| 5,827,834 A | * 10/1998 | Falk et al. ..................... | 514/54 |
| 5,914,314 A | * 6/1999 | Falk et al. ..................... | 514/11 |
| 6,013,641 A | 1/2000 | Lussow et al. | |
| 6,069,135 A | 5/2000 | Falk et al. | |

FOREIGN PATENT DOCUMENTS

| | | |
|---|---|---|
| CA | 1205031 | 5/1986 |
| WO | WO 91/04058 A2 | 4/1991 |
| WO | WO91/04058 | 4/1991 |
| WO | WO 93/16732 A1 | 9/1993 |
| WO | WO 93/16733 A1 | 9/1993 |
| WO | WO 94/23725 A1 | 10/1994 |
| WO | WO 95/30423 A2 | 11/1995 |
| WO | WO96/05845 | 2/1996 |
| WO | WO 96/06622 A1 | 3/1996 |
| WO | WO 97/03699 A1 | 2/1997 |
| WO | WO 97/15330 A1 | 5/1997 |
| WO | WO 97/25051 A1 | 7/1997 |
| WO | WO 98/13024 A2 | 4/1998 |
| WO | WO 98/17320 A1 | 4/1998 |
| WO | WO 98/52590 A2 | 11/1998 |
| WO | WO 99/55230 A1 | 11/1999 |

OTHER PUBLICATIONS

Hamann et al, *Journal of Immunology* 1995, 154(8), 4073–80.*
Han et al. *Journal of Cellular Physiology* 1996, 168(1), 97–104.*
Alho et al., *J. Cell. Biol.*, 108, 1557–1565 (1989).
Kelley et al., *J. Dermatol. Surg. Oncol.*, 16(11), 1039–1042 (1990).
*Martindale The ExtraPharmacopoeia*, Reynolds et al. Editors, The Pharmaceutical Press, London, pp. 234–235 (1982).
*The Merch Index*, Ninth Edition, Merch & Co., Inc., Rahway, New Jersey, p. 407, No. 3058 (1976).
Trabucchi et al., *Int. J. Tiss. Reac.*, VIII(6), 533–544 (1986).
*Webster's Ninth New College Dictionary*, Merriam–Webster Inc., Springfiled, Massachusetts, p. 1256 (1990).
West et al., *Experimental Cell Research*, 183, 179–196 (1989).
Gowland G., et al Marked Enhanced Efficacy of Cyclosporin When Combined With Hyaluronic Acid Evidence From Two T Cell–Mediated Models. *Clinical Drug Investigation*, vol. 11, No. 4, 1996, pp. 245–250, XP000613356.
Toole, B.P. Hyaluronan and its binding proteins, the hyaladherins. *Curr. Opin. Cell. Biol.* 2: 839–844 (1990).
Toole, B.P. Development role of hyaluronate. *Conn. Tiss. Res. 10*: 93–100 (1982).
Entwistle, J. Zhang, S., Yang, B., Wong, C. Hall, C.L., Curpen, G., Mowat M., Greenberg, A.H., and Tutley, E.A. Cloning and characterization of the gene encoding the hyaluronan receptor RHAMM; the role of a secreted isoform in the regulation of focal adhesion formation. *Gene 163*: 233–238 (1995).
Yang, B., Yang, X. Zhang, S., Turley, M., Samuel, S., Savani, R.C., Greenberg, A.H., and Turley, E.A. Overexpression of the hyaluronan receptor RHAMM is transforming, and is required for H–ras transformation. *Cell 82*: 19–28 (1995).
Masellis–Smith, A., Belch, A.R., Mant, M.J., Turley, E.A., and Pilarski., L.M. Hyaluronan–dependent motility of B cells and leukemic plasma cells in multiple myeloma: Alternate usage of RHAMM and CD44. *Blood 81*: 1891–1899 (1996).
Turley, E.A., Belch, A.R., Poppema, S., and Pilarski, L.M. Expression and function of a receptor for hyaluronan–mediated motility (RHAMM) on normal and malignant B lymphocytes. *Blood 81*: 446–453 (1993).

(Continued)

*Primary Examiner*—James O. Wilson
*Assistant Examiner*—Leigh C. Maier
(74) *Attorney, Agent, or Firm*—Pillsbury Winthrop LLP

(57) ABSTRACT

The use of forms of hyaluronic acid having a molecular weight less than about 750,000 daltons selected from the group consisting of hyaluronic acid and pharmaceutically acceptable salts thereof is provided for the same purposes known for using recombinant GM-CSF or G-CSF.

4 Claims, 6 Drawing Sheets

OTHER PUBLICATIONS

Pilarski, L.M., Miszta, H., and Turley, E.A. Regulation expression of a receptor for hyaluronan–mediated motility RHAMM on human thymocytes and T cells. *J. Immunol. 150*: 4292–4302 (1993).

S. K.B., McCoshen, J., Kredentser, J., and Turley, E. The Regulation of Sperm Motlity by a Novel Hyaluronan Receptor. *Fertility and Sterility 61*: 935–940 (1994).

Turely, E.A., Sossain, M.Z., Sorokan, T., Jordan, L.M. and Nagy, J.I. Astrocyte and microglial motility in vitro is funtionally dependent on the hyaluronan receptor RHAMM. *Glia 12*: 68–80 (1994).

Golub, E.S., Green, D.R. Immunology A Synthesis. 2:205, (1991).

Kuby, J. Immunology 3:50; (1997).

Roitt, I., Brostoff, J., Male, D. Immunology 4:2.1 , date 1996.

Weaver, C.H., Hazeltonn, B., Birch, R., Palmer, P., Allen, A., Schwwartzberg, L. and West, W. An analysis of engraftment Kinetics as a function of the CD34 content of peripheral blood progenitor cell collections in 692 patients after the administration of myeloablative chemotherapy. *Blood 86*: 3961–3969 (1995).

Boiron, J.M., Marit, G., Faberes, C., Cony–Makhoul, P., Foures, C., Ferrer, A.M., Cristol, G., Sarrat, A., Girault, D., and Reiffers, J. Collection of peripheral blood stem cells in multiple myeloma following single high–dose cyclophosphamide with and without recombinant human granulocyte–macrophage colony–stimulating factor (rh GM–CSF). *Bone Marrow Transplantation 12*: 49–55 (1993).

Schiller, G., Vescio, R., Freytes, C., Spitzer, G., Sahebi, F., Lee, M., Wu, S.H., Cao, J., Lee, J.C., Hong, C.H. Lichtenstein, A., Lill, M., Hall, J., Berenson, R., and Berenson, J. Transplantation of CD34+ peripheral blood progenitor cells after high–dose chemotherapy for patients with advanced multiple myeloma. *Blood 86*: 390–397 (1995).

* cited by examiner

File: N24.0HR.052
Sample ID: HAFITC CD4PE
Gated Events: 20235
X Parameter: FSC-H FSC-Height (Linear)

Log Data Units: Linear Values
Gate: No Gate
Total Events: 20235
Y Parameter: SSC-H SSC-H (Linear)

| Region | Events | %Gated | %Total | X Mean | X Geo Mean | Y Mean | Y Geo Mean | Px,Py |
|--------|--------|--------|--------|--------|------------|--------|------------|-------|
| R1 | 5091 | 25.16 | 25.16 | 362.40 | 362.02 | 143.68 | 122.43 | 1,2 |
| R2 | 11752 | 58.08 | 58.08 | 460.67 | 458.78 | 183.54 | 174.62 | 1,2 |
| R3 | 1046 | 5.17 | 5.17 | 733.07 | 727.10 | 415.72 | 403.53 | 1,2 |
| R4 | 957 | 4.73 | 4.73 | 703.43 | 697.21 | 1002.78 | 1001.41 | 1,2 |
| R5 | 19853 | 98.11 | 98.11 | 461.99 | 451.20 | 230.98 | 182.21 | 1,0 |

File: N-24 1HR.107  
Sample ID: HAFITC CD4PE  
Gated Events: 29655  
X Parameter: FSC-H FSC-Height (Linear)

Log Data Units: Linear Values  
Gate: No Gate  
Total Events: 29655  
Y Parameter: SSC-H SSC-H (Linear)

| Region | Events | %Gated | %Total | X Mean | X Geo Mean | Y Mean | Y Geo Mean | Px,Py |
|---|---|---|---|---|---|---|---|---|
| R1 | 5929 | 19.99 | 19.99 | 371.93 | 371.42 | 229.53 | 198.56 | 1,2 |
| R2 | 17181 | 57.94 | 57.94 | 449.78 | 448.35 | 194.16 | 184.07 | 1,2 |
| R3 | 1316 | 4.44 | 4.44 | 721.76 | 716.46 | 435.30 | 422.11 | 1,2 |
| R4 | 2809 | 9.47 | 9.47 | 694.70 | 687.82 | 1009.13 | 1007.87 | 1,2 |
| R5 | 29255 | 98.65 | 98.65 | 470.17 | 459.19 | 304.03 | 236.96 | 1,0 |

File: N-24 4HR.161
Sample ID: HAFITC CD4PE
Gated Events: 50000
X Parameter: FSC-H FSC-Height (Linear)

Log Data Units: Linear Values
Gate: No Gate
Total Events: 50000
Y Parameter: SSC-H SSC-H (Linear)

| Region | Events | %Gated | %Total | X Mean | X Geo Mean | Y Mean | Y Geo Mean | Px,Py |
|--------|--------|--------|--------|--------|------------|--------|------------|-------|
| R1 | 15374 | 30.75 | 30.75 | 374.55 | 373.82 | 302.56 | 271.09 | 1,2 |
| R2 | 15359 | 30.72 | 30.72 | 452.13 | 450.52 | 200.91 | 192.99 | 1,2 |
| R3 | 1509 | 3.02 | 3.02 | 764.50 | 759.01 | 477.03 | 465.53 | 1,2 |
| R4 | 12940 | 25.88 | 25.88 | 688.23 | 679.12 | 997.82 | 996.43 | 1,2 |
| R5 | 49787 | 99.57 | 99.57 | 498.00 | 479.12 | 481.11 | 367.27 | 1,0 |

File: N-24 12HRS.215
Sample ID: HAFITC CD4PE
Gated Events: 50000
X Parameter: FSC-H FSC-Height (Linear)

Log Data Units: Linear Values
Gate: No Gate
Total Events: 50000
Y Parameter: SSC-H SSC-H (Linear)

| Region | Events | %Gated | %Total | X Mean | X Geo Mean | Y Mean | Y Geo Mean | Px,Py |
|---|---|---|---|---|---|---|---|---|
| R1 | 11868 | 23.74 | 23.74 | 369.87 | 369.33 | 244.22 | 211.18 | 1,2 |
| R2 | 18416 | 36.83 | 36.83 | 448.85 | 447.39 | 184.25 | 177.16 | 1,2 |
| R3 | 1631 | 3.26 | 3.26 | 770.24 | 765.15 | 485.71 | 472.28 | 1,2 |
| R4 | 15013 | 30.03 | 30.03 | 727.15 | 720.73 | 1017.53 | 1017.07 | 1,2 |
| R5 | 49637 | 99.27 | 99.27 | 524.97 | 502.11 | 476.63 | 337.95 | 1,0 |

File: N-24 24HRS.271
Sample ID: HAFITC CD4PE
Gated Events: 3000
X Parameter: FSC-H FSC-Height (Linear)

Log Data Units: Linear Values
Gate: No Gate
Total Events: 3000
Y Parameter: SSC-H SSC-H (Linear)

| Region | Events | %Gated | %Total | X Mean | X Geo Mean | Y Mean | Y Geo Mean | Px,Py |
|--------|--------|--------|--------|--------|------------|--------|------------|-------|
| R1 | 241 | 8.03 | 8.03 | 372.93 | 372.39 | 200.17 | 172.29 | 1,2 |
| R2 | 2227 | 74.23 | 74.23 | 463.11 | 461.59 | 190.64 | 180.25 | 1,2 |
| R3 | 91 | 3.03 | 3.03 | 736.37 | 729.14 | 428.80 | 415.01 | 1,2 |
| R4 | 273 | 9.10 | 9.10 | 675.01 | 668.46 | 997.55 | 996.15 | 1,2 |
| R5 | 2993 | 99.77 | 99.77 | 484.34 | 476.32 | 284.63 | 223.45 | 1,0 |

File: N-24 72HRS.326
Sample ID: HAFITC CD4PE
Gated Events: 50000
X Parameter: FSC-H FSC-Height (Linear)

Log Data Units: Linear Values
Gate: No Gate
Total Events: 50000
Y Parameter: SSC-H SSC-H (Linear)

| Region | Events | %Gated | %Total | X Mean | X Geo Mean | Y Mean | Y Geo Mean | Px,Py |
|--------|--------|--------|--------|--------|------------|--------|------------|-------|
| R1 | 4631 | 9.26 | 9.26 | 371.76 | 371.26 | 219.42 | 192.19 | 1,2 |
| R2 | 36587 | 73.17 | 73.17 | 468.81 | 467.14 | 205.82 | 199.29 | 1,2 |
| R3 | 2911 | 5.82 | 5.82 | 776.01 | 768.40 | 501.23 | 482.26 | 1,2 |
| R4 | 3399 | 6.80 | 6.80 | 694.12 | 687.24 | 982.82 | 979.60 | 1,2 |
| R5 | 49829 | 99.66 | 99.66 | 496.29 | 485.45 | 289.31 | 240.51 | 1,0 |

METHODS FOR CELL MOBILIZATION USING IN VIVO TREATMENT WITH HYALURONAN (HA)

CROSS-REFERENCE TO RELATED PATENT APPLICATIONS

This application is the U.S. national phase of PCT/CA97/00172, which was filed on Mar. 12, 1997, and which claims the benefit of U.S. provisional patent application 60/013,401, filed on Mar. 14, 1996, and of Canadian Letters Patent No. 2,173,272, filed on Apr. 2, 1996.

FIELD OF THE INVENTION

The invention relates generally to methods using exogenous forms of hyaluronan (HA) for mobilizing hematopoietic cells to the circulation enabling various methods of treatment of humans, including mammals, including methods for obtaining hematopoietic cell transplantation, methods for treating immunosuppression, anemia, osteoporosis, methods for treating cancer, methods for treating allergy and asthma, methods for performing organ transplantation, methods for performing hematopoietic cell transplantation, methods for treating organ/tissue rejection, methods for treating autoimmunity and autoimmune-like conditions, and methods for in vitro fertilization, and in vivo fertility treatments.

BACKGROUND OF INVENTION

Hyaluronan (HA) is a ubiquitous glucosaminoglycan in the extracellular matrix, shown to play a central role in embyrogenesis, inflammation, wound healing, and tumour metastasis.

(Toole, B. P. (1990) *Hyaluronan and its binding proteins, the hyaladherins.* Curr. Opin. Cell. Biol. 2: 839–844.

Toole, B.P. (1982). *Development role of hyaluronate.* Conn. Tiss. Res 10: 93–100.)

Interaction between HA and RHAMM, a receptor for HA-mediated motility are required for motile behaviour of a wide variety of cells including sperm, fibroblasts, astrocytes, microglia and white blood cells.

(Entwistle, J. Zhang, S., Yang, B., Wong, C. Hall, C. L., Curpen, G., Mowat M., Greenberg, A. H., and Turley, E. A. (1995). *Cloning and characterization of the gene encoding the hyaluronan receptor RHAMM; the role of a secreted isoform in the regulation of focal adhesion formation.* Gene 163: 233–238.

Yang, B., Yang, X. Zhang, S., Turley, M., Samuel, S., Savani, R. C., Greenberg, A. H., and Turley, E. A. (1995). *Overexpression of the hyaluronan receptor RHAMM is transforming, and is required for H-ras transformation.* Cell 82: 19–28.

Masellis-Smith, A., Belch, A. R., Mant, M. J., Turley, E. A., and Pilarski., L. M. (1996). *Hyaluronan-dependent motility of B cells and leukemic plasma cells in multiple myeloma: Alternative usage of RHAMM and CD44.* Blood a 87: 1891–1899.

Turley, E. A., Belch, A. R., Poppema, S., and Pilarski, L. M. (1993). *Expression and function of a receptor for hyaluronan-mediated motility (RHAMM) on normal and malignant B lymphocytes.* Blood 81: 446–453.

Pilarski, L. M. Miszta, H., and Turley, E. A. (1993). *Regulation expression of a receptor for hyaluronan-mediated motility RHAMM) on human thymocytes and T cells.* J. Immunol. 150: 4292–4302.

S., K. B., McCoshen, J., Kredentser, J., and Turley, E. (1994). *The Regulation of Sperm Motility by a Novel Hyaluronan Receptor.* Fertility and Sterility 61: 935–940.

Turley, E. A., Sossain, M. Z., Sorokan, T., Jordan, L. M., and Nagy, J. I. (1994) *Astrocyte and microglial motility in vitro is functional dependent on the hyaluronan receptor RHAMM.* Glia 12: 68–80).

The cells that populate the blood are all derived from multipotential (or pluripotential) stem cells present in bone marrow. Multipotential stem cells continually proliferate and renew themselves, but also give rise to common progenitor cells. Once committed, progenitor cells differentiate into immature precursor cells of the various blood cell lineages which, following further differentiation stages, eventually give rise to mature functional blood cells, such as erythrocytes, monocytes, lymphocytes, and polymorphonuclear cells. (Golub, E. S., Green, D. R. (1991) *Immunology A Synthesis,* 2:205; Kuby, J. (1997) *Immunology,* 3:50; Roitt, I., Brostoff, J., Male, D. (1996) *Immunology,* 4:2.1). Terminally differentiated blood cells generally lose their ability to proliferate—indeed mammalian erythrocytes and platelets contain no nuclei—and thus have finite lass Granulocytes may exit only for a matter of hours, whereas human er y remain in circulation for over 100 days. Although some lymphocytes have life-spans measured in years, most are short lived (for example, 3 days-3 weeks). Therefore, to maintain steady-state numbers of particular blood cell types, there must be a continual production of these from e bone narrow. This process is known as haemopoiesis (haematopoiesis) or the haemopoietic process. While much remains to be learned, it is clear that many steps in the haemopoietic process (haemopoiesis) are controlled by certain cytokines (for example, GM-CSF and G-SCF and erythropoietin (EPO)), also known as haemopoietic growth factors, and by microenvironmental factors including stromal cells and extra-cellular matrix components (for example, hyaluronan).

Clinically, the term "mobilization" usually refers to the process whereby cells leave the bone marrow and enter the blood. The mechanism whereby this occurs is not known by those skilled in the art. However, I believe mobilization can be viewed as the stimulation of de-adhesive behaviour by hematopoietic cells.

I believe that under normal circumstances, hematopoietic cells are anchored in their environment by receptors known as adhesion molecules. These adhesion molecules bind to components of the extracellular and cellular matrix within tissues to anchor the cell, or alternatively, to permit its migratory behaviour. Among the receptors thought to be important are those binding HA.

I believe mobilization involves two events: 1) a release from the anchoring interactions (de-adhesion) and 2) the stimulation of migratory behaviour. To reach the circulation from lymphoid tissue or the bone in marrow a cell must "let go" of its anchoring interaction, activate adhesion receptors involved in migration (motile behaviour) and then actually locomote through tissue, penetrate endothelial cell linings and enter the blood vessel (intravasate). HA and receptors for HA are known to be involved in cell migration, motility and de-adhesion.

Most hematopoietic cells are anchored in the bone marrow or other lymphoid tissues. A stimulating/inducing event is required to mobilize them to the circulation as this is an active, not a passive process. Present practice involves administration of a variety of cytokines, often together with chemotherapeutic agents to mobilize hematopoietic cells to the blood. The mechanism for this is unknown. However, stem cell mobilization, the recruitment of hematopoietic stem cells into the blood where they can be easily harvested, is clinically performed using G-CSF and GM-CSF with or without chemotherapy.

(Weaver, C. H., Hazeltonn, B., Birch, R., Palmer, P., Allen, A., Schwwartzberg, L. and West, W. (1995). *An analysis of engraftment kinetics as a function of the CD34 content of peripheral blood progenitor cell collections in 692 patients after the administration of myeloablative chemotherapy.* Blood 86: 3961–3969.

Boiron, J.-M., Marit, G., Faberes, C., Cony-Makhoul, P., Foures, C., Ferrer, A.-M., Cristol, G., Sarrat, A., Girault, D., and Reiffers, J. (1993) *Collection of peripheral blood stem cells in multiple myeloma following single high-dose cyclophosphamide with and without recombinant human granulocyte-macrophage colony-stimulating factor (rh GM-CSF).* Bone Marrow Transplantation 12: 49–55.

Schiller, G., Vescio, R., Freytes, C., Spitzer, G., Sahebi, F., Lee, M. Wu, S.-H., Cao, I., Lee. J. C., Hong, C. H. Lichtenstein, A., Lill, M., Hall, J., Berenson, R., and Berenson, J. (1995) *Transplantation of CD34+peripheral blood progenitor cells after high-dose chemotherapy for patients with advanced multiple myeloma.* Blood 86: 390–397.)

Mobilized peripheral blood stem cell collections (PBSC) resulting from the use of G-CSF or GM-CSF are transplanted into, e.g. a cancer patient. These can be either the total population of the mobilized white blood cells or purified stem cells. Stem cells are those cells able to reconstitute the hematopoietic system of an organism, which requires self renewal of stem cells as well as differentiation to cells of the various hematopoietic lineages. The CD34 marker is characteristic of stem cells. Other cells that are mobilized include polymorphonuclear white blood cells (cells that mediate inflammation and clearance of pathogens), mononuclear white blood cells (lymphocytes and monocytes) and red blood cell progenitors (erythroblasts).

Mobilization of CD34+stem cells is a rapidly expanding clinical technique for obtaining material for autologous or allogeneic hematopoietic transplantation. Mobilization of polymorphs is a valuable adjunct to heavy chemotherapy to maintain innate defense mechanisms. Currently, both methods rely on mobilization by growth factors (G-CSF or GM-CSF) which is expensive, causes bone pain, and has unknown side effects for normal donors. It takes up to about 4 weeks of treatments to collect sufficient material for a transplant. After growth factor treatment, CD34+cells reach a maximum level of 2–4% in blood.

The mature cells of the haemopoietic system include erythrocytes, polymorphonuclear-cells (PMN), lymphocytes, monocytes, macrophages, osteoblasts, osteoclasts, mast cells, and platelets. These all have a limited life-span, and must be replaced as they die. To achieve a balance between cell death and renewal, the bone marrow must not only continuously provide progenitor cells, but also control the commitment of these to the various lineages so that the correct proportions of mature cells are produced. The basic control mechanisms, especially of the earliest stages of haemopoiesis, are as yet poorly understood. There appears to be some compartmentalization of the marrow, and microscopic 'nests' of particular precursor cells have been identified. However, it has been shown that the survival and proliferation of stem and progenitor cells is dependent upon the presence of accessory cells which in vitro form into an adherent 'stromal' layer. In the absence of the stromal layer, stem and progenitor cells die and so it appears the stromal cells support proliferation and differentiation by intercellular interactions including production of growth factors into the extracellular milieu. In culture, stromal cells have been shown to produce GM-CSF, M-CSF, and a megakaryocyte-colony stimulating factor (or molecules functionally equivalent to these). It is widely believed that such growth factors (cytokines) are involved in haemopoiesis, but their exact role(s) in self-renewal of stem cells, differentiation of stem cells into common progenitor cells, and the proliferation and differentiation of committed progenitor cells, remains unclear. More definite roles of these cytokines in the growth stimulation and development of later-stage precursors have been evinced by the use of in vitro colony-forming culture systems introduced by Metcalf and colleagues in the 1970s. In these experimental systems multipotential stem cells, progenitors, or precursors are suspended in the absence of stromal cells in semi-solid agar growth medium. Without the addition of exogenous cytokines, the cells die. However, they can be stimulated to grow, multiply, and differentiate to form colonies of various blood cell lineages by adding into the growth medium dilutions of certain supernatants obtained from activated leukocytes or by addition of the now readily available purified recombinant cytokines including GM-CSF. Furthermore, injection of recombinant cytokines into experimental animals, and into patients in clinical trials to assess therapeutic potential of individual cytokine products, has shown that IL-3, GM-CSF, and G-CSF stimulate the production of white cells such as granulocytes and monocytes, thus lending support for physiological roles of such cytokines. In addition, it has also become apparent that these cytokines not only support the growth and differentiation of immature blood cells, but also in many instances are effector molecules for the functional activation of mature cells.

The molecular cloning of both murine and human homologues of IL-3, GM-CSF, G-CSF, M-CSF, IL-5, and EPO has been accomplished.

Of the four 'granulocyte-macrophage' CSFs, GM-CSF was the first to be isolated and characterized. GM-CSF was shown to induce the proliferation of murine bone marrow— or spleen-derived haemopoietic cells containing granulocyte and macrophage progenitors giving rise to colonies containing mainly granulocyte and macrophage precursors. In this respect, GM-CSF appears to share biological properties with the subsequently characterized IL-3. However, more recent studies suggest that GM-CSF acts on 'later-stage' multipotential cells than IL-3. Also, GM-CSF appears to be less active than IL-3 in stimulating the proliferation of erythroid and megakaryocytic precursors. Nevertheless, like IL-3, GM-CSF can be shown to have activities in mature cells of the granulocyte and macrophage lineages.

GM-CSF (Granulocyte-Macrophage Colony Stimulating Factor) acts directly and selectively on granulocyte/macrophage progenitors to stimulate growth and differentiation in vitro of cells belonging to these lineages, e.g. neutrophils, eosinophils, macrophages. These pleiotropic activities have also been demonstrated for recombinant GM-CSF. Besides regulation of the proliferation and differentiation of the progenitor/precursor cells of the myeloid lineage, GM-CSF has also been shown to activate the functions of mature myeloid cell types. For example, GM-CSF has been found to induce macrophage tumoricidal activity against the malignant melanoma cell line, A375. IFNγ can also behave as a macrophage activating factor, but in contrast to GM-CSF requires an additional secondary stimulus, e.g. bacterial LPS, to evoke tumoricidal activity. In addition, GM-CSF activates macrophages to inhibit the replication of *Trypanosoma cruzi* (a unicellular parasite that is the aetiological agent of Chagas disease, or American trypanosomiasis) and increases respiratory oxidative processes. Furthermore, the replication of HIV-1 in the human monocytic cell line U937 has been shown to be moderately inhibited by GM-CSF, and more effectively by the combination of GM-CSF and IFNγ. These results suggest that GM-CSF could have a potential physiological role in eosinophils and macrophage activation and thus possibly could be used prophylactically or therapeutically against a range of microbial agents that replicate in macrophages.

In neutrophils and eosinophils, GM-CSF stimulates a number of functions. In particular, GM-CSF enhances phagocytosis of bacteria and yeasts by neutrophils. Purified recombinant human GM-CSF has also been shown to enhance the cytotoxic activity of neutrophils and eosinophils against antibody-coated target cells. These observations and others in which the anti-microbial functions of neutrophils and eosinophils are increased by GM-CSF, strongly suggest an important role for this mediator in host defence.

When mice are repeatedly injected intraperitoneally with recombinant murine GM-CSF, there is a rapid and sustained increase in the number and functional activity of peritoneal macrophages, granulocytes (neutrophils and eosinophils) as well as increased numbers of circulating monocytes. (GM-CSF usually takes about two weeks to act.) Marked increases in neutrophil, eosinophil, and monocyte numbers have also been observed following injection of recombinant human GM-CSF into AIDS patients and non-human primates. However, there may be complications associated with GM-CSF therapy. Metcalf and colleagues have shown that transgenic mice containing a constitutively expressed murine GM-CSF gene have pathological lesions soon after birth in various tissues, including lens, retina, and striated muscle, resulting from activated-macrophage infiltration. Thus, chronic macrophage activation in GM-CSF therapeutic schedules should be avoided. (Activated macrophages are known to produce a number of inflammatory mediators including cytokines such as TNFα and IL-1 which may induce tissue damage.)

In contrast to its growth-stimulating effects, GM-CSF can act as a t differentiation factor. Its actions on mature macrophages and neutrophils, for example, might be considered as consequences of its differentiation-inducing capacity. One way to limit the proliferation of tumour cells is to decouple growth-factor-driven self-renewal from growth-factor-induced differentiation. In other words, the more 'differentiated' tumour cells become, the less able they are to multiply. In this regard, GM-CSF has been shown to induce differentiation of the myeloid leukaemic cell line HL60 and suppress its self-renewal. However, in several other studies, GM-SF stimulated the proliferation of HL60 cells. Differentiation can be monitored by measuring expression of various plasma membrane-associated antigens, e.g. CD14 (monocyte/macrophage marker) and CD57 (NK cell marker). These have been reported to be induced by GM-CSF in small cell lung cancer (SCLC) cell lines, suggesting that SCLC has a myeloid cell origin. This would be consistent with a proposal that SCLC arises from macrophage precursors which infiltrate damaged lung tissues, such as occur in heavy smokers. The ready availability of recombinant human GM-CSF and the limited distribution of GM-CSF receptors to cells of the myeloid and possibly erythroid lineages may thus help to define the histological origin of tumours, and suggests alternative therapeutic modalities for the treatment of cancers such as SCLC.

It thus appears that while the use of Granulocyte-macrophage colony stimulating factor (GM-CSF) has been used as a stimulant for the production of stem cells, progenitor cells, precursor cells, accessory cells and macrophages there are a substantial number of disadvantages in its use, those discussed above and the appearance of bone pain, fever, myalgia and erythema in patients to whom cytokines such as GM-CSF and G-CSF were administered, which make the use of GM-CSF and G-CSF not as desirable.

It is therefore an object of this invention to provide the use of another and other compounds which provide similar effects as GM-CSF and G-CSF but with lesser side effects.

It is a further object of this invention to provide such compounds in suitable dosages for effective and safe use.

It is still a further object of this invention to provide improved treatments and regimens of treatment.

It is a further object of the invention to provide a novel use for hyaluronan (HA) for mobilizing cells such as hematopoietic cells.

Further and other objects of the invention will be realized by those skilled in the art from the following summary of invention and detailed description of embodiments thereof.

SUMMARY OF THE INVENTION

The invention provides for a novel use for forms of hyaluronan (HA) for mobilizing hematopoietic cells from bone marrow and other tissues into the circulation.

The invention also provides for the novel use for forms of HA for mobilizing dendritic-type cells from bone marrow and other tissues into the circulation.

The invention also provides for novel use for forms of HA for activating/stimulating stromal cells to facilitate mobilization.

The invention also provides for novel use for forms of HA for releasing cancer cells into the blood.

The forms of HA include hyaluronan and pharmaceutically acceptable salts thereof.

The term "hematopoietic cells" is meant to include all types of hematopoietic cells throughout their differentiation from self-renewing hematopoietic stem cells through immature precursor cells of the various blood lineages to and including the mature functioning blood cells as would be understood by persons skilled in the art.

The term "dendritic-type cells" is meant to include cells in the circulation, the bone marrow and other tissues, including those cell types involved in antigen presentation.

The term "stromal cells" is meant to include the accessory cells that make up the microenvironment of hematopoietic cells, including endothelial cells, adipocytes, fibroblasts, reticular cells, and epithelial cells, and all functionally-like cells.

The terms "individual" or "patient" are meant to encompass all species of mammals. Although examples below may refer to humans, a person skilled in the art would know this is also applicable to other species of mammals.

The term "stimulate" is meant to be equivalent to the term "activate".

The invention further provides for methods for mobilizing hematopoietic cells comprising administering forms of HA in vivo.

The invention further provides a method for generating hematopoietic cells (for example, stem cells) for transplantation comprising administering forms of HA in vivo, and harvesting the cells to be transplanted from the peripheral blood.

The invention further provides a method for mobilizing dendritic-type cells.

The invention further provides a method for activating/stimulating stromal cells.

The invention further provides methods for treating immunosuppression caused by chemotherapy comprising administering forms of HA to individuals who have undergone chemotherapy.

The invention further provides methods for treating immunosuppression and/or immunodeficiency, for example, associated with AIDS, comprising administering forms of HA to individuals who are immunosuppressed or immunodeficient.

The invention further provides methods for treating osteoporosis comprising administering forms of HA to individuals who suffer from osteoporosis.

The invention further provides methods for treating asthma and allergy comprising administering forms of HA to individuals who suffer from asthma and allergy.

The invention further provides methods for treating acquired anemia comprising administering forms of HA to individuals who suffer from acquired anemia (such as blood loss, iron deficient anemia, anemia accruing post-surgery, infection-related anemia, insulin related anemia, low hemoglobin anemias of pregnancy or from red blood cell production). Thus, this invention provides for the administration of forms of HA for the same use as erythropoietin is administered.

The invention further provides methods to release cancer cells from the bone marrow and other tissues into the blood.

According to an aspect of the invention, the administration of hyaluronic acid and pharmaceutically acceptable salts thereof (for example, sodium hyaluronate) is provided for the same use as recombinant G-CSF and/or GM-CSF including the production/release of stem, progenitor and other hematopoietic cells.

According to another aspect of the invention, the administration of hyaluronic acid and pharmaceutically acceptable salts thereof (for example, sodium hyaluronate), enhance the stimulation of hematopoietic cell production/release, e.g. stem cells.

According to another aspect of the invention, the administration of hyaluronic acid and pharmaceutically acceptable salts thereof (for example, sodium hyaluronate), enhance the stimulation of dendritic-type cell production/release and the stimulation of other tissue based antigen-presenting cells production/release.

According to another aspect of the invention, the administration of hyaluronic acid and pharmaceutically acceptable salts thereof (for example, sodium hyaluronate), enhance the stimulation/activation of stromal cells.

According to another aspect of the invention, the administration of hyaluronic acid and pharmaceutically acceptable salts thereof (for sodium hyaluronate) enhance the release of cancer cells from the bone marrow and other tissue into the blood.

In support of my conclusions as to what constitutes my invention, I have conducted tests for which the results are set out as examples herein. Additionally, I have now re-examined tests previously conducted and ongoing tests and determined that my unobvious results, conclusions and thus my invention are substantiated by these additional materials. HA receptors are known to be expressed on nearly all types of hematopoietic cells. Tests have shown that HA receptors able to bind HA are expressed by T lymphocytes, B lymphocytes and monocytes from normal individuals or those with an inflammatory disease (restenosis or inflammatory bowel disease); the receptors involved include RHAMM and CD44. Malignant B cells also express these receptors and utilize them for binding HA as well as in motile behaviour (Masellis Smith et al, BLOOD 1996). Testing has also shown that human thymocytes (immature T cells) have few HA receptors but that interaction with HA causes redistribution of HA receptors (mainly RHAMM) to the cell surface where it is now able to bind HA and to interact with HA to promote thymocyte motility. Testing has also shown that thymocytes have a pool of cryptic HA receptors that are able to bind HA when exposed experimentally, and which can be redistributed to the surface for functional use.

Thus, I have determined that HA is able to upregulate HA receptors, in particular RHAMM, and that these newly expressed receptors actually mediate cell motility. This is an in vitro model of cell mobilization, in this case modeling events that cause thymocytes to leave the solid organ, the thymus, for the blood, analogous to the predicted behavior of HA infused in vivo, as claimed in this invention to cause hematopoietic cells of many types to leave the bone marrow or other tissue and enter the blood. This testing therefore also supports my invention which deals with events in vivo. I believe the infused HA causes redistribution of HA receptors on hematopoietic cells of many types (stem cells and cells at all differentiation stages within hematopoietic lineages) thus increasing their surface density. These receptors then interact with HA to cause de-adhesion and initiation of motile behavior required for migration to the blood (which, I believe, is required for hematopoietic cell mobilization as understood in the clinical terminology). While I believe that this event takes place as described, my invention can be used irrespective of the actual mechanism of mobilization.

Additionally, $CD34^+$ stem cells express HA receptors and can bind HA, providing further in vitro support for their mobilization from the bone marrow to the blood by HA infusion.

Peripheral blood T cells have cryptic HA receptors, are able to weakly bind HA, and undergo motile behavior that is inhibited by antibody to the HA receptor RHAMM even though this receptor is not expressed at an otherwise detectable density of the T cell surface. The fact that RHAMM mediates the motility indicates that HA has upregulated cryptic RHAMM on mature blood T cells as has been demonstrated for immature T cells. It also shows that HA will, I believe, mobilize T cells from lymphoid organs and tissue other than the bone marrow (including the spleen, lymph nodes, Peyer's patches, gut-associated lymphoid tissue and skin associated lymphoid tissue).

Osteoclasts, the cells that dissolve bone and which participate in pathological destruction of bone mass, express the HA receptor CD44, while osteoblasts and osteoprogenitors, the cells that produce bone mass, have only a low amount of CD44. Therefore, I believe, this indicates that osteoclasts and thus bone destruction are preferentially affected by HA L infusion as compared to osteoblasts and osteoprogenitors. Osteoporosis and other conditions characterized by reduced bone mass and resultant increased bone fragility, will thus be modulated by HA infusion. Such modulation will preferentially impact on cells responsible for bone destruction while sparing those responsible for bone production, supporting the use of HA infusion in bone diseases such as osteoporosis.

Further, malignant lymphocytes of the B lineage (lymphoma, multiple myeloma, hairy cell leukemia) express RHAMM and utilize RHAMM to undergo motile behavior. In this case motility is a behavior required for cancer cell spread as well as for migration of cancer cells to and from the bone marrow and other lymphoid organs. Thus, the form of HA, I believe, will mobilize cancer cells, thus facilitating their targeting by therapy.

In many cancers, bone localized cancer cells, or bone metastases are a serious complication of the cancer. Although chemotherapy does reach the bone spaces, it seems inevitable that some regions of the bone are less vascularized than others and that some pockets of malignant disease escape chemotherapeutic agents. A number of studies indicate that tumor cells aggregated into a tumor mass are more drug resistant than those in single cell suspensions. Mobilization of tumor cells into the blood will release them from any tumor aggregates in the marrow or other sites and, I believe, will render them drug sensitive.

Multiple myeloma is a good example of a cancer with large numbers of bone localized malignant cells, while lymphoma and breast cancer include bone metastases which depend on migration from the primary tumor mass through the blood to the bone marrow. The bone marrow is served only by the blood so any traffic to or from the marrow must occur via the blood. In breast cancer, multiple myeloma, and some lymphomas, the HA receptor RHAMM is expressed and identifies circulating cancer cells. In myeloma, the bone marrow localized cancer cells express RHAMM and CD44. For those cancers originating as a solid mass that is usually surgically removed, infusion of HA at the time of surgery, I believe, will prevent surgically dislocated cancer cells from migration through the blood, for example, into the bone or any other tissue site, thus reducing the risk of iatrogenic spread. These cancer cells are now more vulnerable, I believe, to chemotherapy. For those patients with bone tumor cells, I believe, infusion with HA will cause their mobilization into the periphery where they will be more readily attacked, will be exposed to potentially higher doses of therapeutic agents, and where they will now be susceptible to agents that cannot easily enter the bone marrow.

One such possible treatment is the use of combinations of hyaluronan and liposomes and/or any suitable therapeutic agent which, for example, may be bound to hyaluronan. Hyaluronan may be equally used as a targeting and delivery moiety for any suitable agent. See PCT Application WO 91/04058. Treatment may also be by administration of chemotherapeutic agents or other types of therapy.

According to another aspect of the invention, a method is provided whereby a form of HA is infused to a patient to mobilize cancer cells from bone marrow or solid tissues into the blood where the cancer cells exist as single cell suspensions and are rendered more drug sensitive and/or are more effectively attacked by a therapeutic agent and/or removed by some physical procedure such as leukapheresis.

Suitable amounts of the form of hyaluronic acid comprising hyaluronic acid and pharmaceutically acceptable salts thereof may be in the order of between about 1.5 mg/kg of body weight and about 12 mg/kg of body weight, for example, about 6 mg/kg of patient body weight to whom the form of hyaluronic acid is administered (for example, by intravenous infusion or other suitable manner) or a greater amount, such as about 8 mg/kg of patient body weight and about 12 mg/kg of patient body weight, to whom the form of hyaluronic acid is administered. Thus, suitable dosage amounts for a 70 kg person, comprise at least about 105 mg, for example, about 420 mg of the form of hyaluronic acid and for example, 840 mg of the form of hyaluronic acid.

Depending on the cells to be mobilized, different treatment regimens of the dosages may be administered. The following regimens of treatment may be reviewed as follows:

(a) a single dose selected from the above range may, for example, selectively mobilize the desired cell type;

(b) sequential infusions of the same dosage amount of the form of HA (for example, 6 mg/kg given weekly for a month);

(c) sequential infusions with differing amounts in any order. Where patients are given a regimen of treatment over a period of time for example, smaller (lesser) amounts/kg of patient body weight over a period of time (for example, every few days or once a week for a number of weeks), lesser amounts than 6 mg/kg may be used to achieve the same effect. The patient may even be "primed" to start the treatment by giving smaller/lesser dosages which, by themselves, may not be effective for the cell type (but is effective for other cell types). Such priming amounts may for example, be 1.5 mg/kg or 3.0 mg/kg of body weight.

The form of hyaluronic acid may be administered in any suitable carrier such as sterile water or saline. The stimulatory effect usually commences as early as one hour after administration of a form of hyaluronic acid and continues for at least about 72 hours and in cases the effects were still visible after 7 days.

One form of hyaluronic acid and/or pharmaceutically acceptable salts thereof (for example sodium salt) suitable for use with Applicant's invention is an amount having the following specifications/characteristics:

| TESTS | SPECIFICATIONS | RESULTS |
| --- | --- | --- |
| pH | 5.0 to 7.0 at 25 degrees C. | 6.0 |
| Specific Gravity | 0.990 to 1.010 at 25 degrees C. | 1.004 |
| Intrinsic Viscosity | 4.5 to 11.0 dL/g. | 7.07 |
| Molecular Weight | 178,000 to 562,000 daltons | 319,378 daltons |
| Sodium Hyaluronate Assay and Identification | 9.0 to 11.0 mg/mL. Positive | 9.9 mg/ML Positive |

Another such amount may comprise:

| TESTS | SPECIFICATIONS |
| --- | --- |
| 1. Description | White or cream odourless powder |
| 2. Identification (IR Spectrum) | Conforms to Ref. Std. Spectrum |
| 3. pH (1% solution) | 5.0 to 7.0 |
| 4. Loss on Drying | NMT 10% |
| 5. Residue on Ignition | 15.0% to 19.0% |
| 6. Protein Content | NMT 0.1% |
| 7. Heavy Metals | NMT 20 ppm |
| 8. Arsenic | NMT 2 ppm |
| 9. Residual Solvents | |
| a) Formaldehyde | NMT 100 ppm |
| b) Acetone | NMT 0.1% |
| c) Ethanol | NMT 2.0% |
| 10. Sodium Hyaluronate Assay (dried basis) | 97.0 to 102.0% |
| 11. Intrinsic Viscosity | 10.0 to 14.5 dL/g |
| 12. Molecular Weight | 500,000 to 800,000 daltons |
| 13. Total Aerobic Microbial Count (USP 23) | NMT 50 microorganisms/g |
| 14. *Escherichia coli* (USP 23) | Absent |
| 15. Yeasts and Moulds (USP 23) | NMT 50 microorganisms/g |

-continued

| TESTS | SPECIFICATIONS |
|---|---|
| 16. Bacterial Endotoxins (LAL) (USP 23) | NMT 0.07 EU/mg |

Another such amount is available from Hyal Pharmaceuticals Limited and comes in a 15 ml vial of Sodium hyaluronate 20 mg/ml (300 mg/vial—Lot 2F3). The sodium hyaluronate amount is a 2% solution with a mean average molecular weight of about 225,000. The amount also contains water q.s. which is triple distilled and sterile in accordance with the U.S.P. for injection formulations. The vials of hyaluronic acid and/or salts thereof may be carried in a Type 1 borosilicate glass vial closed by a butyl stopper which does not react with the contents of the vial.

The amount of hyaluronic acid and/or salts thereof (for example sodium salt) may also comprise the following characteristics:

a purified, substantially pyrogen-free amount of hyaluronic acid obtained from a natural source having at least one characteristic selected from the group (and preferably all characteristics) consisting of the following:
i) a molecular weight within the range of 150,000–225,000;
ii) less than about 1.25% sulphated mucopolysaccharides on a total weight basis;
iii) less than about 0.6% protein on a total weight basis;
iv) less than about 150 ppm iron on a total weight basis;
v) less than about 15 ppm lead on a total weight basis;
vi) less than 0.0025% glucosamine;
vii) less than 0.0025% glucuronic acid;
viii) less than 0.025% N-acetylglucosamine;
ix) less than 0.0025% amino acids;
x) a UV extinction coefficient at 257 nm of less than about 0.275;
xi) a UV extinction coefficient at 280 nm of less than about 0.25; and
xii) a pH within the range of 7.3–7.9. Preferably, the hyaluronic acid is mixed with sterile water and the amount of hyaluronic acid has a mean average molecular weight within the range of 150,000–225,000 daltons. More preferably, the amount of hyaluronic acid comprises at least one characteristic selected from the group (and preferably all characteristics) consisting of the following characteristics:
i) less than about 1% sulphated mucopolysaccharides on a total weight basis;
ii) less than about 0.4% protein on a total weight basis;
iii) less than about 100 ppm iron on a total weight basis;
iv) less than about 10 ppm lead on a total weight basis;
v) less than 0.00166% glucosamine;
vi) less than 0.0166% glucuronic acid;
vii) less than 0.0166% N-acetylglucosamine;
viii) less than 0.00166% amino acids;
x) a UV extinction coefficient at 257 nm of less than about 0.23;
xi) a UV extinction coefficient at 280 nm of less than 0.19; and
xii) a pH within the range of 7.5–7.7.

Applicants may also use sodium hyaluronate produced and supplied by LifeCore™ Biomedical, Inc., having the following specifications:

| Characteristics | Specification | | | |
|---|---|---|---|---|
| Appearance | White to cream colored particles | | | |
| Odor | No perceptible odor | | | |
| Viscosity Average Molecular Weight | <750,000 Daltons | | | |
| UV/Vis Scan, 190–820 nm | Matches reference scan | | | |
| OD, 260 nm | <0.25 OD units | | | |
| Hyaluronidase Sensitivity | Positive response | | | |
| IR Scan | Matches reference | | | |
| pH, 10 mg/g solution | 6.2–7.8 | | | |
| Water | 8% maximum | | | |
| Protein | <0.3 mcg/mg NaHy | | | |
| Acetate | <10.0 mcg/mg NaHy | | | |
| Heavy Metals, maximum ppm | | | | |
| As  Cd  Cr  Co  Cu | Fe  Pb  Hg  Ni | | | |
| 2.0  5.0  5.0  10.0  10.0 | 25.0  10.0  10.0  5.0 | | | |
| Microbial Bioburden | None observed | | | |
| Endotoxin | <0.07 EU/mg NaHy | | | |
| Biological Safety Testing | Passes Rabbit Ocular Toxicity Test | | | |

Another amount of sodium hyaluronate proposed to be used is sold under the name Hyaluronan HA-M5070 by Skymart Enterprises, Inc. having the following specifications:

| Specifications' Test Results | |
|---|---|
| Lot No. | HG1004 |
| pH | 6.12 |
| Condroitin Sulfate | not detected |
| Protein | 0.05% |
| Heavy Metals | Not more than 20 ppm |
| Arsenic | Not more than 2 ppm |
| Loss on Drying | 2.07% |
| Residue on Ignition | 16.69% |
| Intrinsic Viscosity | 12.75 dl/s (XW: 679,000) |
| Nitrogen | 3.14% |
| Assay | 104.1% |
| Microbiological Counts | 80/g |
| E. coli | Negative |
| Mold and Yeast | Not more than 50/g |

Other forms of hyaluronic acid and/or its salts may be chosen from other suppliers and those described in prior art documents provided they are suitable.

The following references teach hyaluronic acid, sources thereof, and processes for the manufacture and recovery thereof which may be suitable.

U.S. Pat. No. 4,141,973 teaches hyaluronic acid fractions (including sodium salts) having:

"(a) an average molecular weight greater than about 750,000, preferably greater than about 1,200,000—that is, a limiting viscosity number greater than about 1400 cm$^3$/g., and preferably greater than about 2000 cm$^3$/g.;

(b) a protein content of less than 0.5% by weight;

(c) ultraviolet light absorbance of a 1% solution of sodium hyaluronate of less than 3.0 at 257 nanometers wavelength and less than 2.0 at 280 nanometers wavelength;

(d) a kinematic viscosity of a 1% solution of sodium hyaluronate in physiological buffer greater than about 1000 centistokes, preferably greater than 10,000 centistokes;

(e) a molar optical rotation of a 0.1–0.2% sodium hyaluronate solution in physiological buffer of less than $-11 \times 10^3$ degree —cm$^2$/mole (of disaccharide) measured at 220 nanometers;

(f) no significant cellular infiltration of the vitreous and anterior chamber, no flare in the aqueous humour, no haze or flare in the vitreous, and no pathological changes to the cornea, lens, iris, retina, and choroid of the owl monkey eye when one milliliter of a 1% solution of sodium hyaluronate dissolved in physiological buffer is implanted in the vitreous replacing approximately one-half the existing liquid vitreous, said HUA being (g) sterile and pyrogen free and (h) non-antigenic."

Canadian Letters Patent 1,205,031 (which refers to U.S. Pat. No. 4,141,973 as prior art) refers to hyaluronic acid fractions having average molecular weights of from 50,000 to 100,000; 250,000 to 350,000; and 500,000 to 730,000 and discusses processes of their manufacture.

Where high molecular weight hyaluronic acid (or salts) is used, it should be treated to permit administration and ensure no coagulation or blockage.

As there is no toxicity of the form of hyaluronic acid, the form of hyaluronic acid may be administered in doses in excess of 12 mg/kg of body weight, for example, in excess of 1000 mg/70 kg person and even up to amounts of 3000 mg/70 kg person without adverse toxic effects.

Thus, according to another aspect of the invention, a method of treatment is provided comprising the administration to a mammal human) of an effective amount of a form of hyaluronic acid, for example, hyaluronic acid and pharmaceutically acceptable salts thereof (for example, sodium hyaluronate) for enhancing (stimulating) the production/release of hematopoietic cells as measured by phenotypic, physical or chemical properties or any other characteristics used by those skilled in the art to identify a given cell type.

Thus, according to another aspect of the invention, the use of an effective amount of a form of hyaluronic acid is provided for enhancing (stimulating) the production/release of hematopoietic cells as measured by phenotypic, physical or chemical properties or any other characteristics used by those skilled in the art to identify a given cell type.

Thus, according to another aspect of the invention, a method of treatment is provided comprising the administration to a mammal (human) of an effective amount of a form of hyaluronic acid, for example, hyaluronic acid and pharmaceutically acceptable salts thereof (for example, sodium hyaluronate) for enhancing (stimulating) the production/release of dendritic and related antigen presenting cells (dendritic-type cells) as measured by phenotypic, physical or chemical properties or any other characteristics used by those skilled in the art to identify a given cell type.

Thus, according to another aspect of the invention, a method of treatment is provided comprising the administration to a mammal (human) of an effective amount of a form of hyaluronic acid, for example, hyaluronic acid and pharmaceutically acceptable salts thereof (for example, sodium hyaluronate), to activate/stimulate stromal cells in the bone marrow and other tissues.

Thus, according to another aspect of the invention, a method of treatment is provided comprising the administration to a mammal (human) of an effective amount of a form of hyaluronic acid, for example, hyaluronic acid and pharmaceutically acceptable salts thereof (for example, sodium hyaluronate), to release cancer cells from the bone marrow and other tissues to the blood.

Thus, according to another aspect of the invention, the use of an effective amount of a form of hyaluronic acid is provided for enhancing (stimulating) the production/release of dendritic and related antigen presenting cells as measured by phenotypic, physical or chemical properties or any other characteristics used by those skilled in the art to identify a given cell type.

According to another aspect of the invention, the use of an effective amount of a form of hyaluronic acid, for example, hyaluronic acid and pharmaceutically acceptable salts thereof (for example, sodium hyaluronate) is provided for the manufacture of pharmaceutical composition for administration to a mammal (e.g. human) for enhancing (stimulating) the production/release of hematopoietic cells.

According to another aspect of the invention, the use of an effective amount of a form of hyaluronic acid, for example, hyaluronic acid and pharmaceutically acceptable salts thereof (for example, sodium hyaluronate) is provided for the manufacture of pharmaceutical composition for administration to a mammal (e.g. human) in order to activate/stimulate stromal cells in the bone marrow and other tissues.

According to another aspect of the invention, the use of an effective amount of a form of hyaluronic acid, for example, hyaluronic acid and pharmaceutically acceptable salts thereof (for example, sodium hyaluronate) is provided for the manufacture of pharmaceutical composition for administration to a mammal (e.g. human) in order for the release of cancer cells from the bone marrow and other tissues into the blood.

According to another aspect of the invention, the use of an effective amount of a form of hyaluronic acid, for example, hyaluronic acid and pharmaceutically acceptable salts thereof (for example, sodium hyaluronate) is provided for the manufacture of pharmaceutical composition for administration to a mammal (e.g. human) for enhancing (stimulating) the production/release of dendritic and related antigen presenting cells.

According to yet another aspect of the invention, the use of hyaluronic acid and pharmaceutically acceptable salts thereof is provided for stimulating the production/release of hematopoietic cells.

According to yet another aspect of the invention, the use of hyaluronic acid and pharmaceutically acceptable salts thereof is provided for stimulating the production/release of dendritic and related antigen presenting cells.

According to yet another aspect of the invention, the use of hyaluronic acid and pharmaceutically acceptable salts thereof is provided to activate/stimulate stromal cells in the bone marrow and other tissues.

According to yet another aspect of the invention, the use of hyaluronic acid and pharmaceutically acceptable salts thereof is provided to release cancer cells from the bone marrow and other tissues into the blood.

Thus, by administering effective amounts of the forms of hyaluronic acid, patients can be treated with the form of hyaluronic acid which is safe and non-toxic and the patient does not suffer the adverse side effects of recombinant GM-CSF or G-CSF treatment, yet achieves results that are obtained by the administration of recombinant GM-CSF or G-CSF. By administering a regimen of treatment comprising a single dose or a plurality of dosages of hyaluronic acid over a period of time (for example, several weeks) or dosages comprising an amount or amounts which is/are lesser amount(s) followed by amounts which are greater amounts, the patient can be treated. Lesser amounts than the amounts used without priming may be effective in the patient to stimulate the production/release of the cells, the activation, or the release, when the patient is primed. For example, suitable dosage amounts may be 6 mg/kg of patient body weight or 12 mg of the form of hyaluronic acid/kg patient body weight. A suitable regimen may also comprise a suitable amount (for example 1.5 mg of the form of hyaluronic acid/kg patient body weight or 3.0 mg/kg for "priming" purposes also followed by administration of another effective amount (for example, about 6 mg/kg, 10 mg/kg or more after a pre-determined interval or intervals. Another suitable regimen of sustained treatment may be provided as follows:

Week 1: 1.5 mg/kg;
Week 2: (7 days later)—3.0 mg/kg;
Week 3: (7 days later)—6 mg/kg;
Week 4: (7 days later)—12 mg/kg.

The treatment at Week 3 or 4 may be continued in Weeks 5, 6, 7, etc. for as long as required. Any of the treatments may be continued for as long as required.

Thus, the invention provides a novel use for HA as an agent to mobilize hematopoietic and dendritic-type cells. The invention further provides for methods of mobilizing hematopoietic and dendritic-type cells, comprising treatment of subjects with HA. The invention can be used in a variety of applications for which it is necessary or desirable to mobilize hematopoietic and dendritic-type cells, including, but not limited to: obtaining material for transplantation; post-chemotherapy mobilization of granulocytes and monocytes; mobilization of CD4+ T cells from solid lymphoid organs into the blood of AIDS patients.

In an embodiment, mobilization of hematopoietic cells, including polymophonuclear cells, erythroblasts, plasma cells, early stage monocytes, T cells, B cells and stem cells, I believe, was achieved by the sequential intravenous infusion of increasing doses of HA (having a molecular weight of 200,000 to 300,000 daltons determined according to the protein-standard isolated from for example, *Streptomyces*), for over a period of 4 weeks as outlined herein.

This embodiment can be varied and still give equivalent results, and the embodiment can be further optimized for various applications, as indicated herein.

It is anticipated that the administration of HA as smaller or larger fragments could also be used to practise the invention, and their use is included in the invention. HA can be isolated in average MW forms such as the 200,000 to 300,000 MW average amounts used herein, or even smaller molecular weights.

The possibility exists that smaller fragments of HA, less than 200,000 to 300,000, could be more potent in mobilizing hematopoietic and dendritic-type cells for the following reasons. HA breaks down quickly in the circulation and is rapidly cleared by liver endothelial cells. I believe that the HA used, 200,000 to 300,000 MW, is rapidly degraded into smaller fragments that may have increased biological activity in stimulating migratory behaviour, as well as more effective in mediating de-adhesion (release of anchoring). I believe that smaller HA fragments can more easily enter the bone marrow than high MW fragments, which might not be able to traverse through the bone marrow sinus areas where exchange between blood and bone marrow compartments must occur. However, since HA is broken down in vivo the use of larger fragments might be equally effective. The optimum size of HA for infusion can be determined by selecting HA in various MW ranges (e.g. 25,000–50,000, 50,000–100,000 M.W., etc.).

Doses of HA include, but are not limited to, the range of about 1.5 mg/kg to about 12 mg/kg separately, and together in sequential combinations (i.e. multiple infusions of only one concentration, and multiple infusions each at different concentrations).

For example, because 12 mg/kg provided a major effect (see herein), it would be apparent to persons skilled in the art to try increasing doses of HA to find optimal doses for each use. This can be done simply by administering increasing doses of HA to subjects, and analyzing blood samples taken for example, as described herein. Furthermore, rather than sequentially increasing the dose on a weekly basis, HA could be infused weekly (or at other intervals) at an optimal concentration which might be higher or lower than 12 mg/kg depending on the cells to be mobilized. Different frequencies and durations of HA administration can also be examined.

Different routes of administration in addition to intravenous infusion are effective. For example, a "depot" of HA placed subcutaneously or intraperitoneally would provide continuous infusion over a prolonged period and would be a convenient and effective method of providing HA. If HA is administered subcutaneously or intraperitoneally, for example continuous infusion could be achieved and monitoring the subject over time. Alternatively, HA could be administered orally. The invention includes administration of HA by such means and all others as would be understood by persons skilled in the art.

Different protocols of HA administration including variations in size of HA, dosage, route and duration of HA administration will mobilize different populations of hematopoietic and dendritic-type cells. For example, a protocol which optimally mobilizes CD34+ stem cells may be somewhat different from one which is optimal in mobilizing T cells or tumour cells. Thus, the protocol can be optimized for a particular desired application, by administering HA under different conditions, and then monitoring the output of the desired subset of hematopoietic cells in the blood as indicated herein. The time after infusion should be monitored optimal recovery or induction of specific cell populations in the blood, because, as noted in the example herein, the appearance of different cell types occurred sequentially over a period of about a week after infusion. The pattern indicated early (4 hr) release of polymorphonuclear cells and erythroblasts (relatively late stage red cell progenitors which are nucleated), later release of stem cells, small lymphocytes, and plasma cells (24–72 hours) and still later release of monocytoid cells (7 days).

The subjects herein were human subjects. HA would also be effective in primates or other mammals for the mobilization of hematopoietic cells to be used in xenotransplantation or for collecting hematopoietic cells from genetically altered animals (e.g. a pig genetically engineered to express human major histocompatability antigens on their hematopoietic cells).

The use of HA as an agent to mobilize hematopoietic cells is illustrated in the following:

1. HA infusion can be used to generate a source of hematopoietic stem cells for allogeneic or autologous transplantation. Such transplantation is frequently used to restore the hematopoietic system of cancer patients after myeloablative chemotherapy and radiotherapy. Stem cell donors (either the cancer patient prior to chemotherapy or an allogenic donor) can be treated with HA using a generally effective protocol such as the one described herein, or a protocol which has been specifically optimized to yield the maximum number of CD34+ stem cells. PBMC collections can be treated, frozen, and infused into patients using clinical protocols which are well known in the art (for detailed examples of such protocols, see References below:).

(Weaver, C. H., Hazeltonn, B., Birch, R., Palmer, P., Allen, A., Schwwartzberg, L. and West, W. (1995). *An analysis of engraftment kinetics as a function of the CD34 content of peripheral blood progenitor cell col-* lections in 692 patients after the administration of myeloablative chemotherapy. Blood 86: 3961–3969.

Boiron, J.-M., Marit, G., Faberes, C., Cony-Makhoul, P., Foures, C., Ferrer, A.-M., Cristol, G., Sarrat, A., Girault, D., and Reiffers, J. (1993) *Collection of peripheral blood stem cells in multiple myeloma following single high-dose cyclophosphamide with and without recombinant human granulocyte-macrophage colony-stimulating factor* (rh GM-CSF). Bone Marrow Transplantation 12: 49–55.

Schiller, G., Vescio, R., Freytes, C., Spitzer, G., Sahebi, F., Lee, M. Wu, S.-H., Cao, J., Lee. J. C., Hong, C. H. Lichtenstein, A., Lill, M., Hall, J., Berenson, R., and Berenson, J. (1995) *Transplantation of CD34+ peripheral blood progenitor cells after high-dose chemotherapy for patients with advanced multiple myeloma.* Blood 86: 390–397.)

The advantage of using HA as an agent to mobilize stem cells for transplantation over the cytokines now used in the art iii. GM-CSF and G-CSF are numerous. HA has fewer side effects than the cytokines, and appears to act more rapidly, mobilizing a more diverse spectrum of hematopoietic cells, and more of them.

2. HA infusion can be used as a method for supplementary immunotherapy after chemotherapy to mobilize polymorphs and monocytes for front line mechanisms needed in defense against pathogens until recovery from chemotherapy. Currently G-CSF and GM-CSF are used for this purpose, and are administered subcutaneously or intravenously until neutrophil recovery is observed. The advantages to using HA mentioned under paragraph 1 above apply equally here. Treatment of patients with HA as described herein can be substituted for infusion of cytokines in already existing clinical protocols such as those described in the References below:

(Weaver, C. H., Hazeltonn, B., Birch, R., Palmer, P., Allen, A., Schwwartzberg, L. and West, W. (1995). *An analysis of engraftment kinetics as a function of the CD34 content of peripheral blood progenitor cell collections in 692 patients after the administration of myeloablative chemotherapy.* Blood 86: 3961–3969.

Boiron, J.-M., Marit, G., Faberes, C., Cony-Makhoul, P., Foures, C., Ferrer, A.-M., Cristol, G., Sarrat, A., Girault, D., and Reiffers, J. (1993) *Collection of peripheral blood stem cells in multiple myeloma following single high-dose cyclophosphamide with and without recombinant human granulocyte-macrophage colony-stimulating factor* (rh GM-CSF). Bone Marrow Transplantation 12: 49–55.

Schiller, G., Vescio, R., Freytes, C., Spitzer, G., Sahebi, F., Lee, M. Wu, S.-H., Cao, J., Lee. Hg J. C., Hong, C. H. Lichtenstein, A., Lill, M., Hall, J., Berenson, R., and Berenson, J. (1995) *Transplantation of CD34+ peripheral blood progenitor cells after high-dose chemotherapy for patients with advanced multiple myeloma.* Blood 86: 390–397.)

3. HA treatment can also be used as an adjunct to cancer chemotherapy in the following way. In multiple myeloma, other malignancies of the immune system, and metastatic cancer such as breast cancer and small cell lung cancer, malignant cells are/become sequestered or anchored in the bone marrow and/or other tissues. If these malignant cells could be mobilized from the bone marrow or other tissue into the peripherary, they might be more susceptible to chemotherapeutic agents and more effectively killed. A variety of evidence indicates that unanchored cancer cells in suspension have differing susceptibility to a variety of agents than do anchored cancer cells or cancer cells within an aggregate. Higher drug concentration can be achieved in the blood as compared to the bone marrow, and forcing metastatic migrants into the blood would cause their exposure to this higher dose. Treatment with HA prior to the administration of chemotherapeutic agents is expected to optimize the ability of the chemotherapy to target malignant cells. In this regard, the administration of HA will be given prior to the treatment with chemotherapeutic agents such as the combining of the chemotherapeutic agents with HA as taught in WO 91/04058. Such prior administration will be given in effective amounts (such as 6 mg/kg of body weight) preferably at least about 4–24 hours before administration of the chemotherapeutic agent. HA infusion, I believe, will thus facilitate drug-mediated cancer cell kill.

4. HA treatment can also be used to mobilize components of the acquired/adaptive immune response such as T cells and B cells as understood by those skilled in the art. For example, in immunotherapy of AIDS HA can be used as follows. Evidence suggests that CD4+/CD8+ ratios are abnormal mainly in the blood of AIDS patients, but that solid lymphoid tissues such as spleen and lymph node have normal numbers of CD4+ cells. Treatment of patients with HA is expected to mobilize CD4+ T cells from solid lymphoid organs, which would be expected to mediate immune protection to AIDS patients. This will be useful for lymphadenopathy prior to full blown AIDS. Unlike most approaches to treating AIDS, treatment with HA is safe and has no known detrimental side effects. A similar immunodeficiency is frequently exhibited in cancer patients. HA infusion is therefore expected to ameliorate the immunodeficiency. These teachings therefore appear applicable to other conditions involving acquired defects in the adaptive immune response.

5. It is known in the art that proteoglycans and glucosaminoglycans distinguish different sets of mast cells. Treatment with HA, I now believe, mobilizes mast cell progenitors from the bone marrow and peripheral sites (lung, skin, etc.). This would alter the biodistribution of types of mast cells in the blood and tissue and thus modulate symptoms of allergy and asthma. Infusion with HA is expected to mobilize mast cells from tissue into blood and away from local sites of reaction.

6. HA would also be used to mobilize osteoclasts in order to deplete their number within the bone marrow with the aim of reducing their destructive effect on bone mass in osteoporosis and other bone diseases. Based on the properties of osteoprogenitors, osteoblasts and osteoclasts, it is expected that HA will selectively deplete the osteoclasts from the bone marrow, leaving osteoblasts in situ.

7. Administration of HA causes the rapid appearance of erythroblasts in the peripheral blood (see herein). Infusion of HA will therefore be a useful tool in treating acquired anemias. These anemias include iron deficient anemia, anemia occurring post-surgery, infection-related anemia, insulin-related anemia, low hemoglobin anemias of pregnancy, anemia resulting from blood loss or from poor red blood cell production or destruction. Like erythropoietin, HA mobilizes red blood cells to the circulation.

The invention has other uses as would be understood by persons skilled in the art from the following.

According to another aspect of the invention, a method is provided to mobilize any type of susceptible cell from one tissue to another, as a single agent or before/during other clinical procedures, as taught for hematopoietic and other types of normal or malignant cells by the infusion (use) of effective amounts of HA. These cells include non-hematopoietic normal cells and have the potential during at least one differentiation stage in their life cycle to undergo mobilization/migration in vivo, for example the mobilization of oocytes from the ovary to the fallopian tubes. Clinically, this process is invoked for collection of oocytes to be used for in vitro fertilization. HA will, I believe, improve oocyte release when used in conjunction with other clinical procedures used by those skilled in the art. The invention also provides a method of HA infusion with or without other treatments known to those skilled in the art, to improve fertility treatments in vivo.

According to another aspect of the invention a method is provided to mobilize hematopoietic cells before and during harvesting of tissue to be used for organ transplantations by the infusion of effective amounts of HA. The harvested tissue will, I believe, be free of passenger lymphocytes and other hematopoietic and dendritic-type cells, that have been shown to stimulate organ rejection. It also provides a method to use ex vivo HA perfusion to mobilize hematopoietic and dendritic-type cells out of an ex-vivo organ that has already been harvested from the donor. This includes, for example, the in vivo perfusion of tissues in a legally dead organ donor in vivo prior to harvesting of the organ, e.g. heart, liver/lung, kidney or other tissues required for organ transplantation. This also includes HA infusion before and during perfusion ex-vivo that occurs after an organ to be used for transplantation has been harvested from the organ donor prior to grafting it into the recipient host. This method of infusing HA before and during perfusion regimens in vivo and/or ex-vivo will, I believe, substantially improve depletion of donor ru hematopoietic cells as compared to perfusion solutions without HA as used by those skilled in the art, and thus improve graft survival. This includes a form(s) of HA as taught in the invention including forms of low molecular weight HA (smaller forms).

According to another aspect of the invention, a method is provided using HA infusion to treat host individuals about to receive an organ transplant prior to and during the transplantation procedure by the infusion (use) of effective amounts of HA. This will mobilize any host hematopoietic or dendritic-type cells out of/away from the site of organ transplant. This will delay the ability of host hematopoietic or dendritic-type cells to home to the transplanted organ and force them to remain in the circulation, thus maximizing the effects of subsequent or simultaneous treatment with immunosuppressive agents.

According to another aspect of the invention, a method is provided using HA infusion to mobilize hematopoietic cells and dendritic-type cells away from/out of an organ graft that shows signs of immunologic rejection, as understood by those skilled in the art by the infusion (use) of effective amounts of HA. Infusion of HA with or without immunosuppressive regimens used by those skilled in the art, will stimulate the migration/mobilization out of the threatened organ graft of infiltrating host hematopoietic cells that attack an organ graft. This mobilization, as taught in the invention, will force the graft-infiltrating hematopoietic and dendritic-type cells into the blood where they are more effectively immunosuppressed by agents used by those skilled in the art.

According to another aspect of the invention, a method is provided to optimize immunosuppressive regimens used by those skilled in the art to dampen or inhibit immune responses, for example in organ or hematopoietic cell transplantation, in autoimmune and autoimmune-like conditions, and in asthma/allergy, or in any condition involving damaging immune reactivity. Such method comprises administration to a patient of an effective amount of HA to optimize the immunosuppressive regimens used in patients to dampen or inhibit immune responses. Levels of immunosuppressive agents in the blood exceed those in other tissues. Mobilization of rejecting or autoreactive hematopoietic cells, particularly lymphocytes and dendritic-type cells, from the tissues at risk or autoimmunity or rejection into the blood will reduce-halt the immunologic attach and facilitate immunosuppression of the attacking hematopoietic and dendritic-type cells mobilized into the blood by increasing their exposure to immunosuppressive agents.

According to another aspect of the invention, a method to maximize chemotherapeutic kill of hematopoietic and dendritic-type cells by infusing HA before and during the cytoreductive therapy administered prior to an autologous or allogeneic hematopoietic cell transplant in, for example, cancer patients such method comprises administration to a patient of an effective amount of HA to maximize chemotherapeutic kill of hematous poretic and dendritic-type cells in patients benefiting from same. Infused HA will mobilize hematopoietic and dendritic-type cells into the blood where they become more susceptible to the cytoreductive agents used by those skilled in the art, including chemotherapy and/or irradiation regimens, based on evidence that single cells are more vulnerable to these agents than are cells in contact with other cells and microenvironmental factors (i.e. stromal cells and extracellular matrix components) (i.e. in an anchored microenvironmental or as a cellular aggregate).

Embodiments of the invention will now be illustrated with reference to the following Figures in which:

DETAILED DESCRIPTION OF FIGURES

Figure 1:
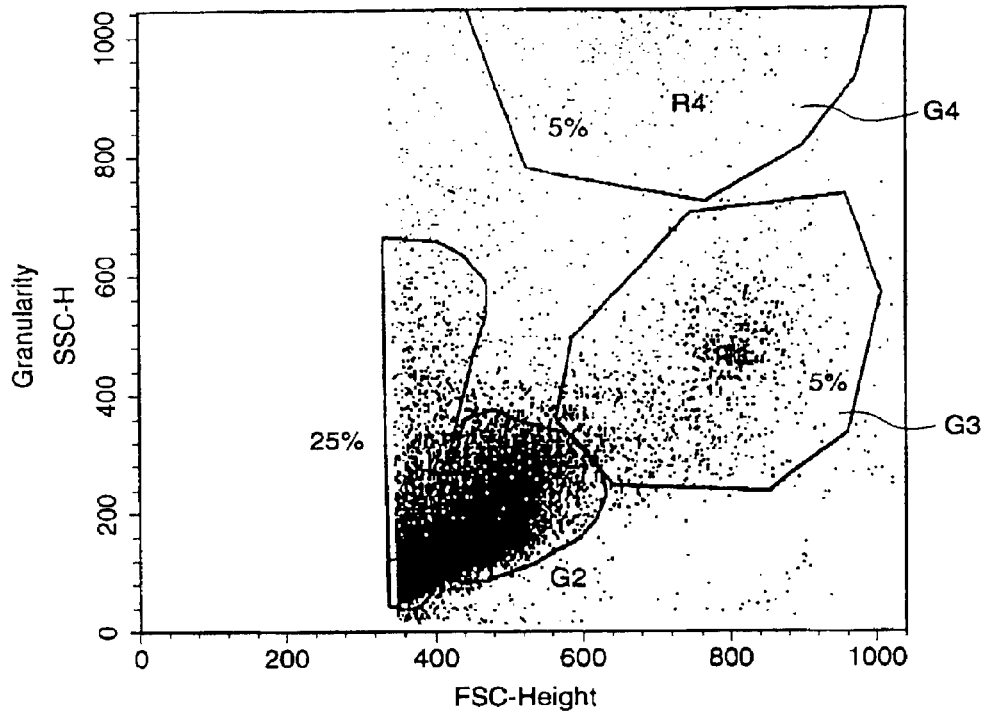
FIGS. 1–6 depict the results of the flow cytometry technique of cell analysis that identifies cells, in this case, the white blood cells (the red cells were specifically excluded from the analyzed cells) according to their cell surface characteristics (using known antibodies to detect them) and their sizes, taken from healthy individuals who were administered the form of hyaluronic acid, sodium hyaluronate, at time "0" and from whom blood was drawn at time: 0 (FIG. 1); 1 hour after administration of sodium hyaluronate (FIG. 2); 4 hours after administration (FIG. 3); 12 hours after administration (FIG. 4); 24 hours after administration of sodium hyaluronate (FIG. 5); and 72 hours after administration (FIG. 6). [The blood cells used had been previously purified using centrifugation over Ficoll-Paque™ (commercially available from Pharmacia).]
Figure 1:
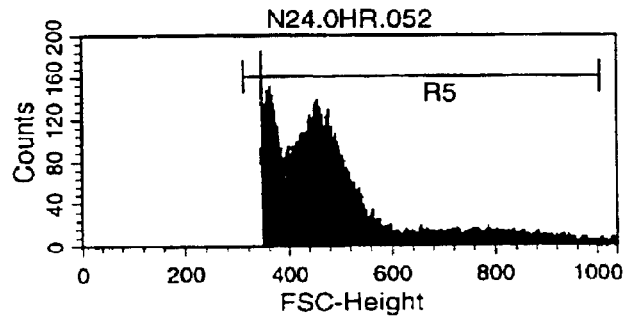

Thus, FIG. 1 (and the other FIGS. 2–6) provide plots of cell characteristics including granularity (plotted vertically) and forward scatter (FSC-height) relating to size of cells (plotted horizontally). The Plot shows different fractions labeled $G_1$ to $G_4$ (corresponding to $R_1$ to $R_4$ with $R_5$ being the entire field) of which $G_4$ is the one of concern displaying changes in the number of larger granular cells which I have concluded have exited/emigrated the bone marrow. ($R_5$ is the entire field of analyzed cells.) I have concluded that the presence of the large granular cells is indicative of generalized mobilization that includes stem cells (which are small and therefore have a low light scatter and were not specifically identified in this assay) and other hematopoietic cells.

The cells that fall into the region identified as G4 are those that have high light scatter properties. The high forward scatter indicates large physical size. The high side scatter indicates increased granularity. In normal individuals, peripheral blood mononuclear cells include very few cells in this size fraction, in the range of about 0–3%. Infusion of HA caused a greatly increased number of cells to appear in this size fraction, indicating to me that they were newly emigrated into the blood. Normally, most cells with high light scatter are bone marrow residents. As an example, plasma cells, the cells that are high rate secretors of antibody, are in this size fraction, and appear in the blood only in pathological conditions such as in multiple myeloma. The expression of CD19, a B cell marker present on some plasma cells, and the high scatter indicated to me that HA had mobilized bone marrow plasma cells into the blood of the normal volunteers. The majority of normal plasma cells are bone marrow localized. After HA infusion, the number of cells with high scatter increased dramatically over the 72 hour study period.

It is therefore clear that the percentage of the cells in $G_4$ relative to all the cells in the field. ($R_5$) which comprises $G_1$ (which corresponds to $R_1$), $G_2$ (which corresponds to $R_2$), $G_3$ (which corresponds to $R_3$), and $G_4$ which corresponds to $R_4$) and the others found in $R_5$ not previously accounted for are with respect to:

FIG. 1 (after 0 hours)→5% calculated as $(G_4) \times 100\%$    ($R_5$)

Figure 2:
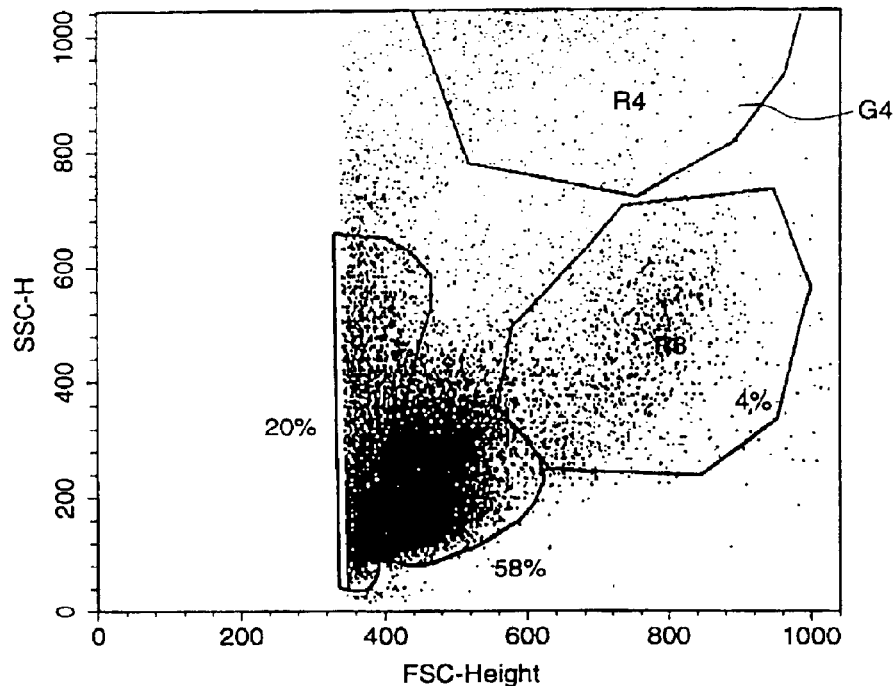
Figure 2:
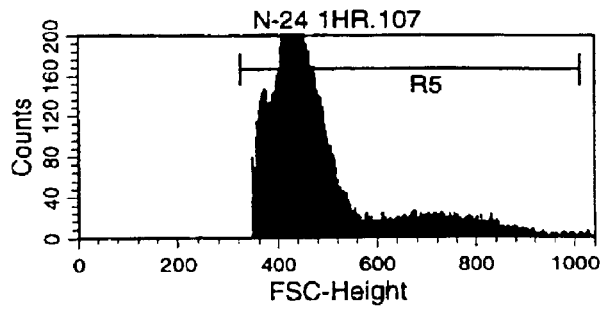

FIG. 2 (after 1 hour) 9% calculated as $(G_4) \times 100\%$    ($R_5$)

Figure 3:
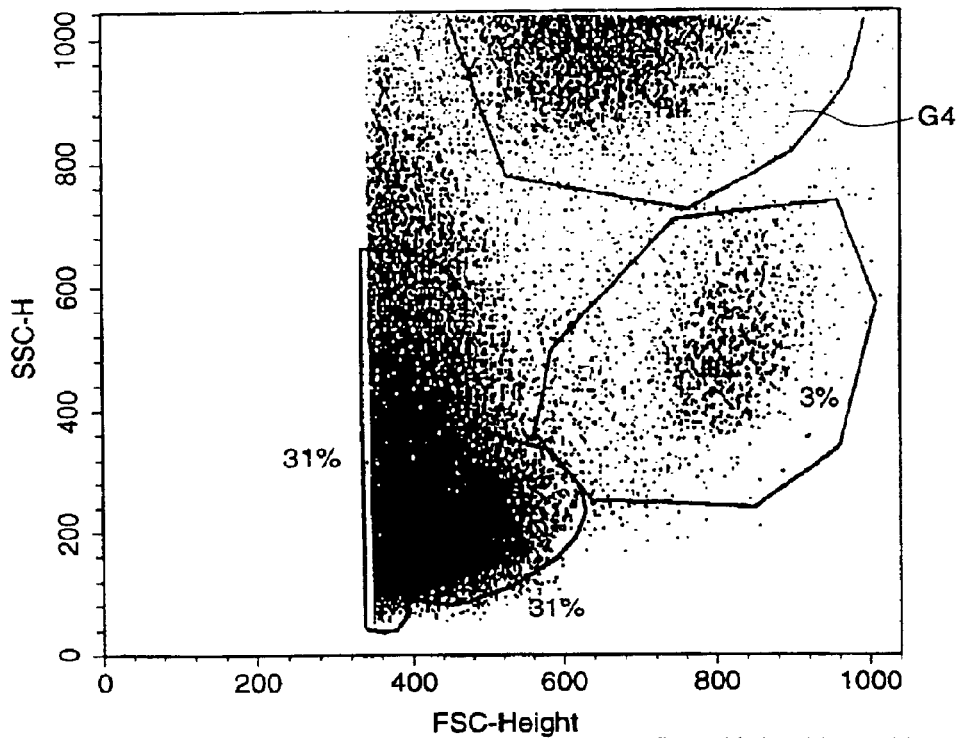
Figure 3:
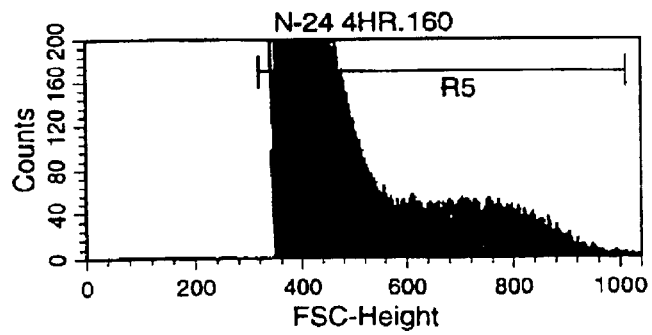

FIG. 3 (after 4 hours) 26% calculated as $(G_4) \times 100\%$    ($R_5$)

Figure 4:
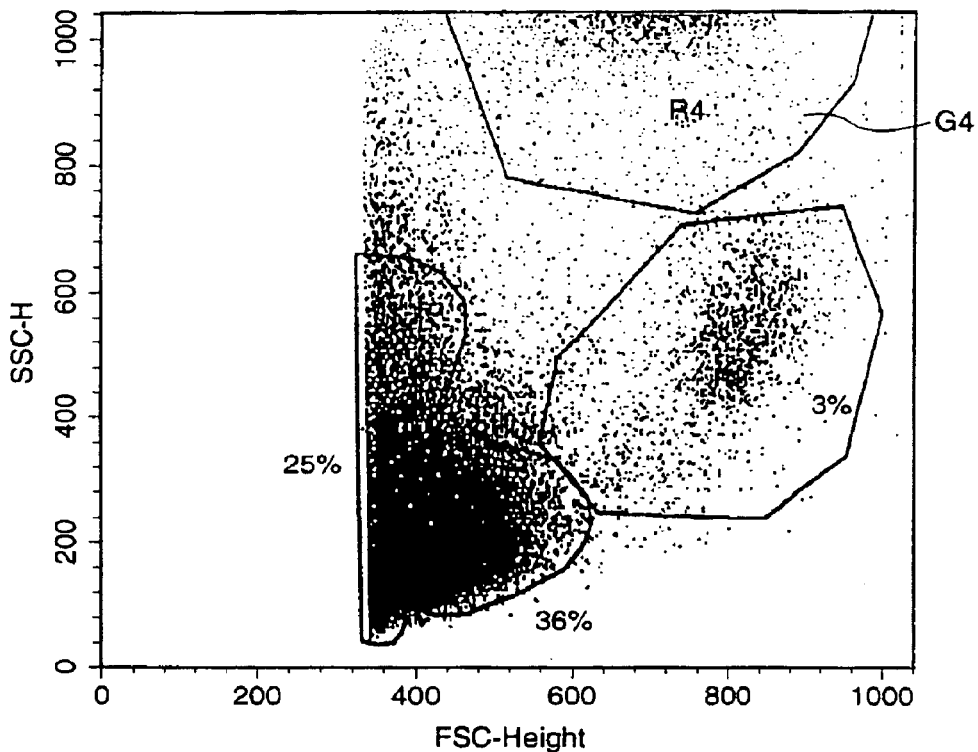
Figure 4:
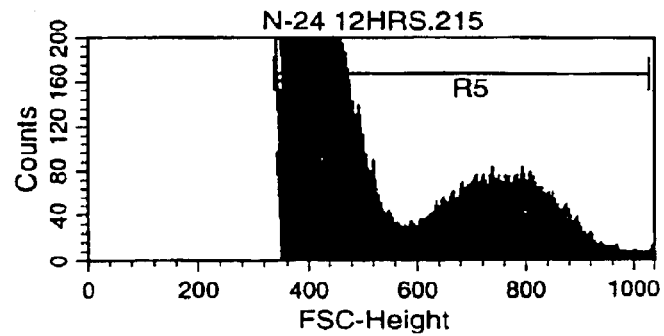

FIG. 4 (after 12 hours)) 30% calculated as $(G_4) \times 100\%$    ($R_5$)

Figure 5:
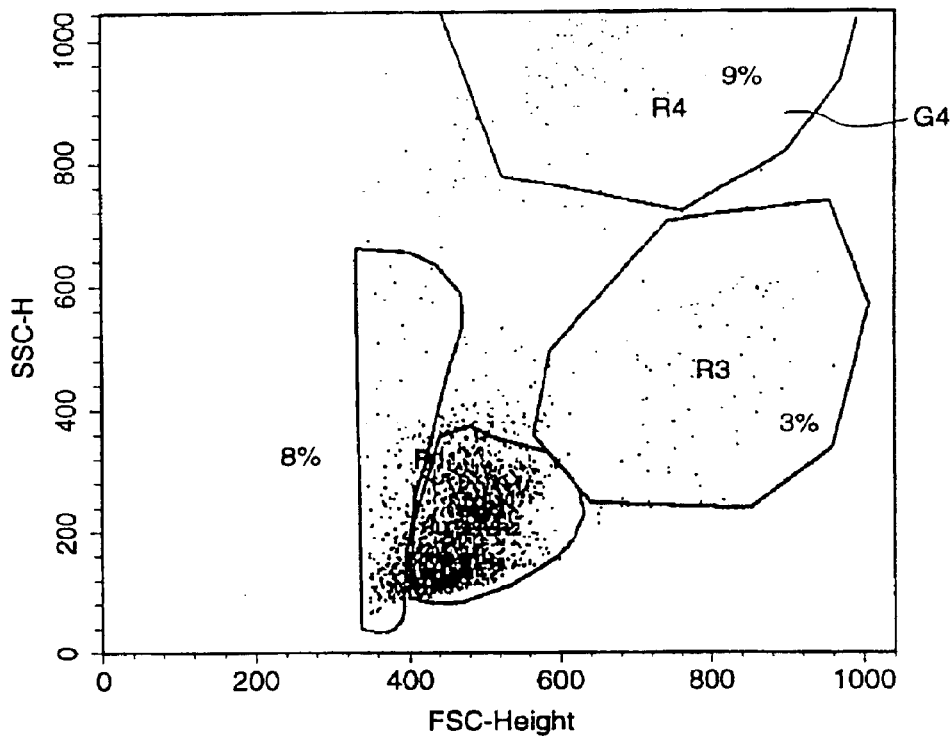
Figure 5:
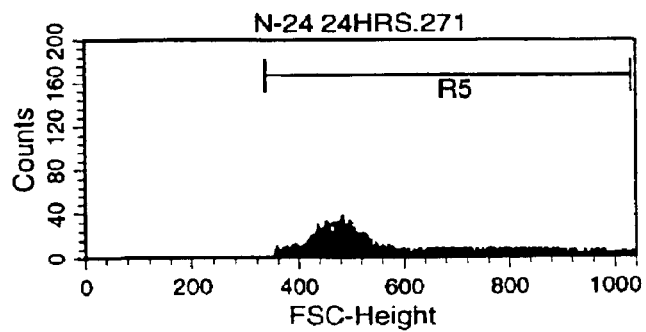

FIG. 5 (after 24 hours) 9% calculated as $(G_4) \times 100\%$    ($R_5$)

Figure 6:
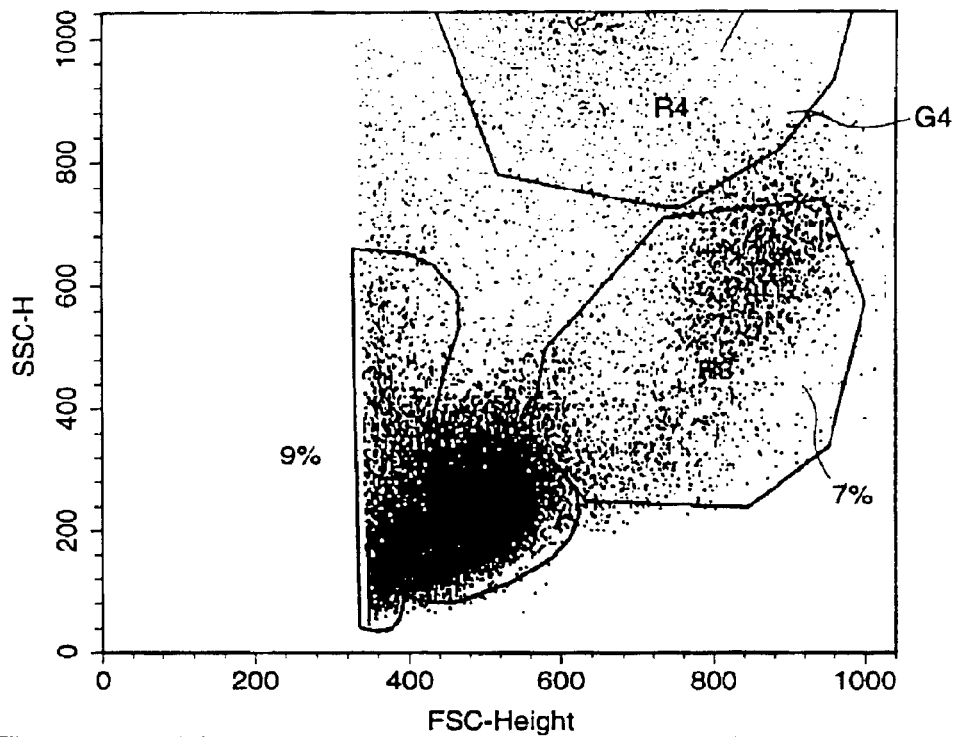
Figure 6:
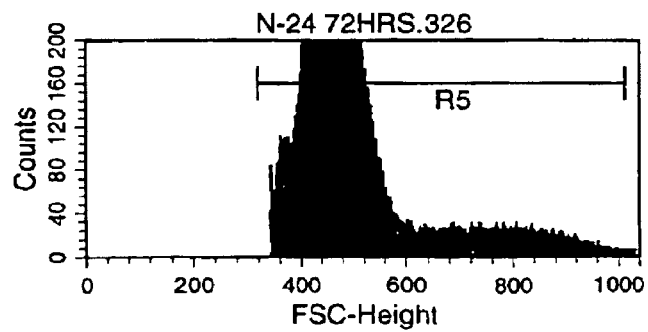

FIG. 6 (after 72 hours)) 6% calculated as $(G_4) \times 100\%$    ($R_5$)

(Each of FIGS. 1–6 is accompanied by supporting data and chart plotting. Counts v. FSC-Height)

The data shown is based on examples wherein the amount of sodium hyaluronate equals or exceeds 1.5 mg/kg of body weight per patient (for example, 6 mg/kg and 12 mg/kg which provide very similar results). Before administering the 6 mg/kg and 12 mg/kg amounts, patients were administered 1.5 mg/kg and 3.0 mg/kg as discussed.

The characteristics of the sodium hyaluronate used with the protocols are set out below:

| "A" | | |
|---|---|---|
| TESTS | SPECIFICATIONS | RESULTS |
| pH | 5.0 to 7.0 at 25 degrees C. | 6.0 |
| Specific Gravity | 0.990 to 1.010 at 25 degrees C. | 1.004 |
| Intrinsic Viscosity | 4.5 to 11.0 dL/g. | 7.07 |
| Molecular Weight | 178,000 to 562,000 daltons | 319,378 daltons |
| Sodium Hyaluronate Assay and Identification | 9.0 to 11.0 mg/mL. Positive | 9.9 mg/ML Positive |

Another amount may comprise:

| TESTS | SPECIFICATIONS |
|---|---|
| 1. Description | White or cream odourless powder |
| 2. Identification (IR Spectrum) | Conforms to Ref. Std. Spectrum |
| 3. pH (1% solution) | 5.0 to 7.0 |
| 4. Loss on Drying | NMT 10% |
| 5. Residue on Ignition | 15.0% to 19.0% |
| 6. Protein Content | NMT 0.1% |
| 7. Heavy Metals | NMT 20 ppm |
| 8. Arsenic | NMT 2 ppm |
| 9. Residual Solvents | |
|    a) Formaldehyde | NMT 100 ppm |
|    b) Acetone | NMT 0.1% |
|    c) Ethanol | NMT 2.0% |
| 10. Sodium Hyaluronate Assay (dried basis) | 97.0 to 102.0% |
| 11. Intrinsic Viscosity | 10.0 to 14.5 dL/g |
| 12. Molecular Weight | 500,000 to 800,000 daltons |
| 13. Total Aerobic Microbial Count (USP 23) | NMT 50 microorganisms/g |
| 14. *Escherichia coli* (USP 23) | Absent |
| 15. Yeasts and Moulds (USP 23) | NMT 50 microorganisms/g |
| 16. Bacterial Endotoxins (LAL) (USP 23) | NMT 0.07 EU/mg |

The following protocol was followed for administering the sodium hyaluronate identified under "A" in the preceding pages and the drawing of blood from the patients to whom the sodium hyaluronate was administered.

Four healthy non-smoking female volunteers and four healthy non-smoking male volunteers were given, at different times (at least 7 days between dosages) the following dosages:

(A) 1.5 mg/kg body weight, intravenous infusion of sterile 1% hyaluronic acid solution.

(B) 3.0 mg/kg body weight, intravenous infusion of sterile 1% hyaluronic acid solution.

(C):6.0 mg/kg body weight, intravenous infusion of sterile 1% hyaluronic acid solution.

(D) 12.0 mg/kg body weight, intravenous infusion of sterile 1% hyaluronic acid solution.

(The hyaluronic acid solution was as described herein as "A" in the preceding pages of this specification.)

In each case, a total volume of 250 ml was infused. Therefore, the 1% hyaluronic acid solution as required was diluted with an appropriate volume of 0.9% sodium chloride solution. The infusion was over a period of 120 minutes.

Each of the dosages was administered in an ascending manner (1.5 mg/kg, 3.0 mg/kg, 6.0 mg/kg, and 12.0 mg/kg) to each of the individuals with at least 7 days between doses. The individuals were asked to engage in normal activity for the first four hours after drug administration avoiding both vigorous exertion and complete rest.

Blood samples were drawn from each person at time intervals of 0, 1, 4, 12, 24 and 72 hours after the administration of each of the dosages.

The cells in the drawn samples were analyzed by a known cell analysis technique, termed flow cytometry. FIGS. 1–6 illustrate the results of analyzing the purified white blood cells in the blood samples taken from the individuals after 0, 1, 4, 12, 24, and 72 hours after administration of 12 mg/kg of body weight of the sodium hyaluronate by intravenous infusion of the individuals, after purification. (Red cells have been excluded from the analysis of these tests.)

Area $G_4$ displays cells with high light scatter, herein termed large cells, in the blood samples. Cells that have these properties include plasma cells, polymorphonuclear cells (such as granulocytes, neutrophils, and the like) or osteoclasts. Normally, at time, t=0 hours [at infusion], only small amounts of these cells are present in normal blood (less than 3% of the total of white cell [$R_5$] population).

After administration of 12 mg of sodium hyaluronate/kg of body weight, their presence increases. [Increases were also visible when lower amounts of HA/kg were infused but are not shown.]

After 12 mg/kg infusion into one normal individual, blood sample was taken, purified and analyzed with the following results:

| time (t) hours | % of cells that are large cells |
|---|---|
| 1 | 9.47 |
| 4 | 25.88 |
| 12 | 30.03 |
| 24 | 9.10 |
| 72 | 6.80 |

These large cells, which are detected at relatively high numbers in the blood after HA infusion, I have concluded are emigrants from the bone marrow. Because their scatter properties are identical to those of late stage B cells and plasma cells that arise in malignant conditions (e.g. multiple myeloma), I have also concluded that they include plasma cell migrants from the bone marrow, the major site of: plasma cells in the body. Phenotypic characterization of these large cells arising after HA infusion indicates that they express a low density of the B cell marker CD19, also consistent with their identity as plasma cells. If plasma cells are stimulated to migratory behavior by HA infusion, other cell types, in particular stem cells, will also be stimulated into migratory behavior. Thus these large plasma-like cells, I have concluded, are indicators of hematopoietic cell migration from the bone marrow into the blood. HA upregulates HA receptors as well as sending signals to the cell that activate motogenic behavior and ultimately migration out of the marrow into the ail blood.

Thus, instead of using recombinant GM-CSF with its adverse effects, the individual may now receive a form of hyaluronic acid (without the same side effects). Because of a lack of toxicity, greater amounts than 12 mg/kg of body weight may be administered to a patient for the effect. I have also found that an amount of 6 mg sodium hyaluronate/kg of body weight administered to an individual has the similar effect as the administration of 12 mg sodium hyaluronate/kg of body weight. Lesser amounts than 6 mg/kg of administered HA achieved detectable effects on the cell types in the peripheral blood. During this 4 week infusion protocol the earlier doses impacted on the later doses. For example, the 0.1 mg/kg and 3 mg/kg of patient weight "primes" the patient so that lesser amounts of the form of hyaluronic acid may be suitable to be effective to stimulate the production/release of the hematopoietic cells at subsequent doses.

The Example discussed above has also been specified as follows:

According to the Example, HA (a 1% solution from *Streptomyces*, of molecular weight 200,000–300,000, with less than 0.1% protein contaminants [Hyal Pharmaceutical Corporation, Mississauga, Ontario] described as "A" previously of the application, was infused intravenously into each of 6 normal adult volunteers weekly for 4 weeks. The dosage of HA given on each of the 4 weeks was:

Week 1: 1.5 mg of HA per kg of body weight,
Week 2: 3 mg of HA per kg of body weight,
Week 3: 6 mg of HA per kg of body weight,
Week 4: 12 mg of HA per kg of body weight.

The dosage was infused over a period of approximately 2 hours each week.

Each week, blood samples were taken at time zero (immediately before infusion), and at time points 1 hour, 4 hours, 12 hours, 24 hours and 72 hours after infusion was initiated. White blood cells were purified using standard clinical laboratory techniques, and then analyzed for their physical properties (size and granularity) using flow cytometry methods which are well established in the art. Cells were stained with monoclonal antibodies (tagged with a phycoerythrin, which gives orange staining) which are accepted in the art to detect B cells (CD19), T cells (CD4 and CD8) and monocytes (CD14). The ability to bind HA was detected by exposing cells to FITC-labeled HA (which gives green staining). White blood cell types were defined by these properties as is widely accepted in the art of clinical analysis.

Results

The infusion with HA caused the appearance in blood of white blood cell types and numbers not seen in normal blood. The following changes were observed in samples of blood taken after HA infusion.

Increase in Polymorphonuclear Cells

A subset of large cells with high side scatter (SSC), having the properties of highly granular polymorphonuclear cells increased from about 4% to about 30% of total peripheral blood cells. This increase occurred most markedly on weeks 3 and 4 (the 6 and 12 mg/kg doses), and over the time period from 4 to 12 hours after infusion.

Appearance of Erythroblasts

At the 4 hour time point on week 4 (the 12 mg/kg dose), the blood sample had many red cells aggregating on the interface of the Ficoll-Paque™ purification gradient. This does not occur in normal blood, but is frequent in bone marrow and some blood samples taken after chemotherapy for multiple myeloma, and is usually due to the presence of erythroblasts that were increased in number after chemotherapy. I therefore conclude that erythroblasts were mobilized by infusion of HA.

Appearance of Plasma Cells

At the 72 hour time point, on week 4 (the 12 mg/kg dose), there were large numbers of large granular cells with a dim CD19 (a B cell marker) expression, and high HA binding, the characteristics of plasma cells. Normally, plasma cells are not found in blood, and the majority of plasma cells in normal individuals are located in the bone marrow. This suggests that HA has released plasma cells from the bone marrow. This does not appear to occur for cytokine mobilizations, suggesting that HA mobilizes cellular types not usually mobilized.

Appearance of Early Stage Monocytes

On week 4, at time zero, there are large numbers (20 to 40%) of cells having the scatter properties expected for monocytes. However, use of a monocyte marker did not detect them, and unlike monocytes, they did not bind HA. Since they are present only at time 0, and only on week 4, they are late migrants to the blood resulting from the previous infusion of HA. They appear to be early stage monocytes.

Increase in Proportion of Small Cells

At the 24–72 hour time points for weeks 3 and 4 (the 6 and 12 mg/kg doses), most samples had a marked increase in the proportion of small cells. These include T cells, B cells and probably hematopoietic stem cells.

The unusual populations in the purified white blood cells after HA infusion, I have thus concluded, are cells that have migrated to the blood as a result of exposure to HA. In one example this is due to a competition effect that mediates release from the bone marrow matrix, as well as an activation of cell migration by HA (which is known to be a central player in cell motility). The patterns indicate early (4 hr) release/migration of polymorphs and erythroblasts (relatively late stage red cell progenitors which are nucleated), later release of stem cells, small lymphocytes, and plasma cells (24–72 hours) and very late release of monocytoid cells (7 days). The most dramatic changes occur at week 4 and tend to be progressively increasing over the 4 week period. Thus many infusions of HA mobilize more cells, and more types of cells than only one infusion, and higher concentrations mobilize more cells and cell types than lower doses. The mobilization at 4 hours and later correlates with the presence in circulation and in the body of smaller fragments of HA. Digested HA may be a better mobilizing agent than large HA. As little as one exposure to the lowest dose of HA alters purified white blood cell populations indicative of mobilization. However, it happens more reproducibly at higher doses or after more than one infusion. Close inspection of the data taken at weeks 1 and 2 (after infusion of 1.5 or 3 mg/kg concentrations of HA) indicated that at least mobilization of large cells occurred. Inspection of data of untreated normal people and of the time 0 data for the 3 subsequent cycles of treatment indicated that the effects of HA were cumulative as the proportion of high scatter cells gradually increased over the 4 week period.

As many changes can be made to the embodiments without departing from the scope of the invention, it is intended that all material contained herein be interpreted as illustrative of the invention and not in a limiting sense.

The embodiments of the invention in which an exclusive property or privilege is claimed are as follows:

1. A method of transplanting stem cells into a patient in need of stem cell transplantation comprising:

(a) administering to a stem cell donor an effective amount of a form of hyaluronic acid selected from the group consisting of hyaluronic acid and pharmaceutically acceptable salts thereof having a molecular weight less than about 750,000 daltons to increase the concentration of stem cells in the blood of the donor;

(b) harvesting the stem cells to be transplanted from peripheral blood of the donor; and (c) transplanting the harvested stem cells into the patient.

2. The method of claim 1 wherein the donor is the same as the patient.

3. The method of claim 1 wherein the donor is not the same as the patient.

4. A method of mobilizing cells prior to and during harvesting tissue to be used for organ transplantation comprising:

(a) perfusing the tissues of an organ donor with a dosage consisting essentially of a mobilizing effective amount of hyaluronic acid and pharmaceutically acceptable salts thereof having a molecular weight less than 750,000 daltons, wherein the perfusing occurs prior to harvesting of the tissue; and (b) harvesting the tissue to be used for organ transplantation.

* * * * *